(12) United States Patent
Curvers et al.

(10) Patent No.: US 9,944,956 B2
(45) Date of Patent: Apr. 17, 2018

(54) METHODS AND MICROBIAL CULTURES FOR IMPROVED CONVERSION OF LIGNOCELLULOSIC BIOMASS

(71) Applicant: DIREVO Industrial Biotechnology GmbH, Cologne (DE)

(72) Inventors: Simon Curvers, Cologne (DE); Vitaly Svetlitchnyi, Cologne (DE)

(73) Assignee: DIREVO Industrial Biotechnology GmbH, Cologne (DE)

(*) Notice: Subject to any disclaimer, the term of this patent is extended or adjusted under 35 U.S.C. 154(b) by 203 days.

(21) Appl. No.: 14/412,320

(22) PCT Filed: Jul. 5, 2013

(86) PCT No.: PCT/EP2013/064256
§ 371 (c)(1),
(2) Date: Dec. 31, 2014

(87) PCT Pub. No.: WO2014/009273
PCT Pub. Date: Jan. 16, 2014

(65) Prior Publication Data
US 2015/0140602 A1    May 21, 2015

Related U.S. Application Data

(60) Provisional application No. 61/669,962, filed on Jul. 10, 2012.

(30) Foreign Application Priority Data

Jul. 10, 2012  (EP) .................................... 12175673

(51) Int. Cl.
| | | |
|---|---|---|
| C12P 7/56 | (2006.01) | |
| C12P 39/00 | (2006.01) | |
| C12N 1/20 | (2006.01) | |
| C12N 1/22 | (2006.01) | |
| C12P 7/06 | (2006.01) | |
| C12P 7/10 | (2006.01) | |
| C12P 7/14 | (2006.01) | |
| C12P 7/40 | (2006.01) | |
| C12R 1/01 | (2006.01) | |

(52) U.S. Cl.
CPC .................. *C12P 7/56* (2013.01); *C12N 1/20* (2013.01); *C12N 1/22* (2013.01); *C12P 7/065* (2013.01); *C12P 7/10* (2013.01); *C12P 7/14* (2013.01); *C12P 7/40* (2013.01); *C12P 39/00* (2013.01); *C12R 1/01* (2013.01); *C12P 2201/00* (2013.01); *Y02E 50/16* (2013.01); *Y02E 50/17* (2013.01); *Y02E 50/343* (2013.01)

(58) Field of Classification Search
None
See application file for complete search history.

(56) References Cited

U.S. PATENT DOCUMENTS 6,555,350 B2    4/2003  Ahring

FOREIGN PATENT DOCUMENTS

| WO | 2007134607 A1 | 11/2007 |
|---|---|---|
| WO | 2009108908 A1 | 9/2009 |
| WO | 2010075213 A2 | 7/2010 |

OTHER PUBLICATIONS

PCT/EP2013/064256 International Search Report dated Nov. 13, 2013.
Svetlitchnyi et al. "Single-step ethanol production from lignocellulose using novel extremely thermolphilic bacteria." Biotechnology for Biofuels, 2013, 6:31.

*Primary Examiner* — Suzanne M Noakes
*Assistant Examiner* — Stephen M Chong
(74) *Attorney, Agent, or Firm* — Wagenknecht IP Law Group PC

(57) ABSTRACT

The present technology pertains to methods and microbial co-cultures for converting lignocellulosic biomass to biofuels and/or other carbon-based chemicals. Aspects of the present disclosure relate to novel consolidated bioprocessing (CBP) methods by which the efficiency of the production of biofuels and/or other carbon-based chemicals from cellulosic biomass-containing materials can be increased. In particular, the present disclosure provides numerous microbiological co-cultures for increasing the efficiency of ethanol and/or lactic acid production from biomass.

13 Claims, 22 Drawing Sheets

DDGS: distillers dried grains and solubles; BP: beet pulp; SCB: sugar cane bagasse; CORNST: corn stalks; CORNPL: corn plants; MISC: miscanthus grass; SORG: sweet sorghum; SPR: spruce wood; STEX: steam explosion pretreatment Neighbor-joining tree based on 16S rRNA gene sequence comparisons of isolated *Caldicellulosiruptor* sp. strains and selected bacteria

**Neighbor-joining tree based on 16S rRNA gene sequence comparisons of isolated *Thermoanaerobacter* sp. strains and selected bacteria**

FIGURE 8

**16SrDNA consensus sequence for *Caldicellulosiruptor spec.* DIB004C (SEQ ID NO. 1)**

```
TTACGACTTC ACCCCAATCA TCAGCCCCAC CTTCAACACA GCTTAACCTG TGTCTTCAGG      60
TGTTGCTGAC TCTCATGGTG TGACGGGCGG TGTGTACAAG GCCCGGGAAC GTATTCACCG     120
CGGCATGCTG ATCCGCGATT ACTAGCGATT CCGACTTCAT GCAGGCGAGT TGCAGCCTGC     180
AATCCGAACT GGGGGTGCTT TTTTGGGATT CGCTCCGGCT CGCGCCTTCG CACGCCCTCT     240
GTAGCACCCA TTGTAGCACG TGTGTAGCCC AGGGCATAAG GGGCATGATG ATTTGACGTC     300
ATCCCCACCT TCCTCCGCCT CATCGACGGC AGTCCCCTTA GAGTGCCCAC CATTACGCGC     360
TGGCAACTAA GGGCAGGGGT TGCGCTCGTT GCGGGACTTA ACCCAACATC TCACGACACG     420
AGCTGACGAC AACCATGCAC CACCTGTGTC CGGGCTCCTG CTCTCATCGA ACAGGCACCC     480
CACCCTTTCG GGCAGCTCCC CGGCATGTCA AGCCCTGCTA AGGTTCTTCC CGTTGCTTCC     540
AATTAAACCA CATGCTCCAC CGCTTGTGCG GGCCCCCGTC AATTCCTTTG AGTTTCAACC     600
TTGCGGCCGT ACTCCCCAGG CGGGATGCTT ATTGTGTTAA CTACGGCACG GAGGAGTCCT     660
TCTCCCCCAC ACCTAGCATC CATCGTTTAC AGCGTGGACT ACCAGGGTAT CTAATCCTGT     720
TCCCTCCCCA CCCTTTCGTC CCTCAGCCTC ACTTACGCTC CACACGGCCC CCTTCGCCAC     780
TGGTGTTCCT CCCGATATCT ACGCATTTCA CCGCTACACC GGGAATTCCG CCGTCCTCTC     840
CCGCACTCAA GCTATGCAGT ATTAAGCGCA ATCCTTAGGT TGAGCCTAAG GCTTTCACGC     900
TTAACTCGCA TAGCCGCCTA CGCACCCTTT ACGCCCAGTA ATTCCGGACA ACGCTCGCCA     960
CCTACGTATT ACCGCGGCTG CTGGCACGTA GTTAGCCGTG GCTTTTTAAA CGGGTACTAT    1020
CTCCTACTTC TCCCCGTCCA AAGAGGTTTA CACCCCGAAG GGCTTCTTCC CTCACGCGGC    1080
GTCGCTGCGT CAGGCTTCCG CCCATTGCGC AAGATTCCCC GCTGCTGCCT CCCGTAGGAG    1140
TGTGGGCCGT GTCTCAGTCC CACTGTGGCC GTACACCCTC TCAGCCGGC TACCCGTCGT    1200
CGCCTTGGTA GGCCGTTACC CCACCAACTA GCTGATGGGC CGCGAGCCCA TCCCCAGCCA    1260
GTATACCCTC CCCGCCTACC CTTTCACCAC ATCACCATCC GATCACGTCC TCCCATCCGG    1320
TATTAGCAGC CCTTTCGAGC TGTTATCCCC GTGCTGGGGG TAGGTTGCTC ACGTGTTACT    1380
CACCCGTCCG CCGCTA                                                    1396
```

Figure 9

**16SrDNA consensus sequence for *Caldicellulosiruptor* sp. DIB041C (SEQ ID NO. 2)**

```
CTCAGGACGA ACGCTGGCGG CGTGCCTAAC GCATGCAAGT CGAGCGGAGG TAGCCATGAA    60
GGTGAAGAGC TGGAGTGGCT ATCTTAGCGG CGGACGGGTG AGTAACACGT GAGCAACCTA   120
CCCTCAGCAC GGGGATAACA GCTCGAAAGG GCTGCTAATA CCCGATGGGA CCACGGCATC   180
GCATGATGTT GTGGTGAAAG GGTAGCCGTG GAGGCTATAC CGGCTGGGGA TGGGCTCGCG   240
GCCCATCAGC TAGTTGGTGG GGTAACGGCC TACCAAGGCT ACGACGGGTA GCCGGCCTGA   300
GAGGGTGGTC GGCCACAGTG GGACTGAGAC ACGGCCCACA CTCCTACGGG AGGCAGCAGC   360
GGGGAATCTT GCGCAATGGG CGAAAGCCTG ACGCAGCGAC GCCGCGTGAG GGAGGAAGCC   420
CTTCGGGGTG TAAACCTCTT TGGACGGGGA GAAGGAGGAG ATAGTACCCG TTTAAAAAGC   480
CACGGCTAAC TACGTGCCAG CAGCCGCGGT AATACGTAGG TGGCGAGCGT TGTCCGGAAT   540
TACTGGGCGT AAAGGGTGCG TAGGCGGCTA TGCAAGTTAA GCGTGAAATC TTGGGGCTCA   600
ACCCCAAGGC TGCGCTTAAT ACTGCATAGC TTGAGTGCGG GAGAGGACGG CGGAATTCCC   660
GGTGTAGCGG TGAAATGCGT AGATATCGGG AGGAACACCA GTGGCGAAGG CGGCCGTCTG   720
GACCGTAACT GACGCTGAGG CACGAAAGCG TGGGGAGCGA ACAGGATTAG ATACCCTGGT   780
AGTCCACGCT GTAAACGATG GATGCTAGGT GTGGGGGAGA AGGACTCCTC CGTGCCGTAG   840
TTAACACAAT AAGCATCCCG CCTGGGGAGT ACGGCCGCAA GGTTGAAACT CAAAGGAATT   900
GACGGGGGCC CGCACAAGCG GTGGAGCATG TGGTTTAATT CGAAGCAACG CGAAGAACCT   960
TACCAGGGCT TGACATGCCG GGAACCTGCC CGAAAGGGTG GGGTGCCTGC GCGATGAGTG  1020
CAGGAGCCCG GACACAGGTG GTGCATGGTT GTCGTCAGCT CGTGTCGTGA GATGTTGGGT  1080
TAAGTCCCGC AACGAGCGCA ACCCCTGCCC TTAGTTGCCA GCACGTAATG GTGGGCACTC  1140
TAAGGGGACT GCCGCCGATG AGGCGGAGGA AGGTGGGGAT GACGTCAAAT CATCATGCCC  1200
CTTATGCCCT GGGCTACACA CGTGCTACAA TGGGTGCTAC AGAGGGTTGC GAAGGCGCGA  1260
GCCGGAGCTA ATCCCAAAAA AGCACCCCCA GTTCGGATTG CAGGCTGCAA CTCGCCTGCA  1320
TGAAGTCGGA ATCGCTAGTA ATCGCGGATC AGCATGCCGC GGTGAATACG TTCCCGGGCC  1380
TTGTACACAC CGCCCGTCAC ACCATGAGAG TCAGCAACAC CTGAAGACAC AGGGCAGCTG  1440
TGTTGAAGGT GGGGCTGATG ATTGGGTGA AGTCGTAACA                         1580
```

Figure 10

**16SrDNA consensus sequence for *Caldicellulosiruptor* sp. DIB087C (SEQ ID NO. 3)**

```
TCAGGACGAA CGCTGGCGGC GTGCCTAACG CATGCAAGTC GAGCGGAGAT GGTGGTTGAA    60
GGTGATGAGC TGGAGGCTGC CATCTTAGCG GCGGACGGGT GAGTAACACG TGAGCAACCT   120
ACCCCCAGCA CGGGGATAAC AGCTCGAAAG GGCTGCTAAT ACCCGATGGG ACCACGTCAT   180
CGCATGGTGA TGTGGTGAAA GGGTAGCCGG GGAGGCTATA CTGGCTGGGG ATGGCTCGC    240
GGCCCATCAG CTAGTTGGTG GGGTAACGGC TCACCAAGGC GACGACGGGT AGCCGGCCTG   300
AGAGGGTGTA CGGCCACAGT GGGACTGAGA CACGGCCCAC ACTCCTACGG GAGGCAGCAG   360
CGGGGAATCT TGCGCAATGG GCGGAAGCCT GACGCAGCGA CGCCGCGTGA GGGAAGAAGC   420
CCTTCGGGGT GTAAACCTCT TTGGACGGGG AGAAGTAGGA GATAGTACCC GTTTAAAAAG   480
CCACGGCTAA CTACGTGCCA GCAGCCGCGG TAATACGTAG GTGGCGAGCG TTGTCCGGAA   540
TTACTGGGCG TAAAGGGTGC GTAGGCGGCT ATGCCAGTTA AGCGTGAAAG CCTTAGGCTC   600
AACCTAAGGA TTGCGCTTAA TACTGCATAG CTTGAGTGCG GGAGAGGACG GGGAATTCC    660
CGGTGTAGCG GTGAAATGCG TAGATATCGG GAGGAACACC AGTGGCGAAG GCGGCCGTCT   720
GGACCGTAAC TGACGCTGAG GCACGAAAGC GTGGGGAGCG AACAGGATTA GATACCCTGG   780
TACTCCACGC TGTAAACGAT GGATGCTAGG TGTGCGGGAG AACGACTCTT CCGTCCCGTA   840
GTTAACACAA TAAGCATCCC GCCTGGGGAG TACGGCCGCA AGGTTGAAAC TCAAAGGAAT   900
TGACGGGGGC CCGCACAAGC GGTGGAGCAT GTGGTTTAAT TCGAAGCAAC GCGAAGAACC   960
TTACCAGGGC TTGACATGCC GGCGACCTCC CCGAAACGGT GGCGTGCCTG TTCGATGACA  1020
GCAGGAACCC GGACACAGGT GGTGCATGGT TGTCGTCAGC TCGTGTCGTG AGATGTTGGG  1080
TTAAGTCCCG CAACGAGCGC AACCCCTGCC CTTAGTTGCC AGCGGGTAAT GGTGGGCACT  1140
CTAAGGGGAC TGCCGTCGAT GAGGCGGAGG AAGGTGGGGA TGACGTCAAA TCATCATGCC  1200
CCTTATGCCC TGGGCTACAC ACGTGCTACA ATGGGTGCTA CAGAGGGCGT GCGAAGGCGC  1260
GAGCCGGAGC GAATCCCAAA AAAGCACCCC CAGTTCGGAT TGCAGGCTGC AACTCGCCTG  1320
CATGAAGTCG GAATCGCTAG TAATCGCGGA TCAGCATGCC GCGGTGAATA CGTTCCCGGG  1380
CCTTGTACAC ACCGCCCGTC ACACCATGAG AGTCAGCAAC ACCTGAAGAC ACAGGTTAAG  1440
CTGTGTTGAA GGTGGGCTG ATGATTGGGG TGAAGTCGTA A                      1481
```

FIGURE 11

**16SrDNA consensus sequence for *Caldicellulosiruptor spec.* DIB101C (SEQ ID NO. 4)**

```
CCTGTGTCTT CAGGTGTTGC TGACTCTCAT GGTGTGACGG GCGGTGTGTA CAAGGCCCGG    60
CAACGTATTC ACCCCGGCAT CCTGATCCGC CATTACTAGC GATTCCGACT TCATGCAGCC   120
CAGTTGCACC CTCCAATCCG AACTGGGGGT CCTTTTTTCC GATTCCCTCC CCCTCCCGCC   180
TTCGCACGCC CTCTGTAGCA CCCATTGTAG CACGTGTGTA GCCCAGGGCA TAAGGGGCAT   240
GATGATTTGA CGTCATCCCC ACCTTCCTCC GCCTCATCGA CGGCAGTCCC CTTAGAGTGC   300
CCACCATTAC GCGCTGGCAA CTAAGGGCAG GGGTTGCGCT CGTTGCGGGA CTTAACCCAA   360
CATCTCACGA CACGAGCTGA CGACAACCAT GCACCACCTG TGTCCGGGCT CCTGCTCTCA   420
TCGAACAGGC ACCCCACCCT TTCGGGCAGG TCCCCGGCAT GTCAAGCCCT GGTAAGGTTC   480
TTCGCGTTGC TTCGAATTAA ACCACATGCT CCACCGCTTG TGCGGGCCCC CGTCAATTCC   540
TTTGAGTTTC AACCTTGCGG CCGTACTCCC CAGGCGGGAT GCTTATTGTG TTAACTACGG   600
CACGGAGGAG TCCTTCTCCC CCACACCTAG CATCCATCGT TTACAGCGTG GACTACCAGG   660
GTATCTAATC CTGTTCGCTC CCCACGCTTT CGTGCCTCAG CGTCAGTTAC GGTCCAGACG   720
GCCGCCTTCG CCACTGGTGT TCCTCCCGAT ATCTACGCAT TTCACCGCTA CACCGGGAAT   780
TCCGCCGTCC TCTCCCGCAC TCAAGCTATG CAGTATTAAG CGCAATCCTT AGGTTGAGCC   840
TAAGGCTTTC ACGCTTAACT CGCATAGCCG CCTACGCCC CTTTACGCCC AGTAATTCCG   900
GACAACGCTC GCCACCTACG TATTACCGCG GCTGCTGGCA CGTAGTTAGC CGTGGCTTTT   960
TAAACGGGTA CTATCTCCTA CTTCTCCCCG TCCAAAGAGG TTTACACCCC GAAGGGCTTC  1020
TTCCCTCACG CGGCGTCGCT GCGTCAGGCT TCCGCCCATT GCGCAAGATT CCCCGCTGCT  1080
GCCTCCCGTA GGAGTGTGGG CCGTGTCTCA GTCCCACTGT GGCCGTACAC CCTCTCAGGC  1140
CGGCTACCCG TCGTCGCCTT GGTAGGCCGT TACCCCACCA ACTAGCTGAT GGGCCGCGAG  1200
CCCATCCCCA GC                                                      1212
```

Figure 12

**16SrDNA consensus sequence for *Caldicellulosiruptor* sp. DIB103C (SEQ ID NO. 5)**

```
CGACTTCACC CCAATCATCA GCCCCACCTT CAACACAGCT TAACCTGTGT CTTCAGGTGT    60
TGCTGACTCT CATGGTGTGA CGGGCGGTGT GTACAAGGCC CGGGAACGTA TTCACCGCGG   120
CATGCTGATC CGCGATTACT AGCGATTCCG ACTTCATGCA GGCGAGTTGC AGCCTGCAAT   180
CCGAACTGGG GGTGCTTTTT TGGGATTCGC TCCGGCTCGC GCCTTCGCAC GCCCTCTGTA   240
GCACCCATTG TAGCACGTGT GTAGCCCAGG GCATAAGGGG CATGATGATT TGACGTCATC   300
CCCACCTTCC TCCGCCTCAT CGACGGCAGT CCCCTTAGAG TGCCCACCAT TACGCGCTGG   360
CAACTAAGGG CAGGGGTTGC GCTCGTTGCG GGACTTAACC CAACATCTCA CGACACGAGC   420
TGACGACAAC CATGCACCAC CTGTGTCCGG GCTCCTGCTC TCATCGAACA GGCACCCCAC   480
CCTTTCGGGC AGGTCCCCGG CATGTCAAGC CCTGGTAAGG TTCTTCGCGT TGCTTCGAAT   540
TAAACCACAT GCTCCACCGC TTGTGCGGGC CCCCGTCAAT TCCTTTGAGT TTCAACCTTG   600
CGGCCGTACT CCCCAGGCGG GATGCTTATT GTGTTAACTA CGGCACGGAG GAGTCCTTCT   660
CCCCCACACC TAGCATCCAT CGTTTACAGC GTGGACTACC AGGGTATCTA ATCCTGTTCG   720
CTCCCCACGC TTTCGTGCCT CAGCGTCAGT TACGGTCCAG ACGGCCGCCT TCGCCACTGG   780
TGTTCCTCCC GATATCTACG CATTTCACCG CTACACCGGG AATTCCGCCG TCCTCTCCCG   840
CACTCAAGCT ATGCAGTATT AAGCGCAATC CTTAGGTTGA GCCTAAGGCT TTCACGCTTA   900
ACTCGCATAG CCGCCTACGC ACCCTTTACG CCCAGTAATT CCGGACAACG CTCGCCACCT   960
ACGTATTACC GCGGCTGCTG GCACGTAGTT AGCCGTGGCT TTTTAAACGG GTACTATCTC  1020
CTACTTCTCC CCGTCCAAAG AGGTTTACAC CCCGAAGGGC TTCTTCCCTC ACGCGGCGTC  1080
GCTGCGTCAG GCTTCCGCCC ATTGCGCAAG ATTCCCCGCT GCTGCCTCCC GTAGGAGTGT  1140
CCCCCGTGTC TCAGTCCCAC TGTGCCCCTA CACCCTCTCA GCCCCCCTAC CCGTCCTCCC  1200
CTTGGTAAGC CGTTACCCCA CCAACTAGCT GATGGGCCGC GAGCCCATCC CCA         1253
```

Figure 13

**16SrDNA consensus sequence for *Caldicellulosiruptor* sp. DIB104C (SEQ ID NO. 6)**

```
GACTTCACCC CAATCATCAG CCCCACCTTC AACACAGCTT AACCTGTGTC TTCAGGTGTT    60
GCTGACTCTC ATGGTGTGAC GGGCGGTGTG TACAAGGCCC GGGAACGTAT TCACCGCGGC   120
ATGCTGATCC GCGATTACTA GCGATTCCGA CTTCATGCAG GCGAGTTGCA GCCTGCAATC   180
CGAACTGGGG GTGCTTTTTC GGGATTCGCT CCGGCTCGCG CCTTCGCACG CCCTCTGTAG   240
CACCCATTGT AGCACGTGTG TAGCCCAGGG CATAAGGGGC ATGATGATTT GACGTCATCC   300
CCACCTTCCT CCGCCTCATC GACGGCAGTC CCCTTAGAGT GCCCACCATT ACGCGCTGGC   360
AACTAAGGGC AGGGGTTGCG CTCGTTGCGG GACTTAACCC AACATCTCAC GACACGAGCT   420
GACGACAACC ATGCACCACC TGTGTCCGGG CTCCTGCTCT CATCGAACAG GCACCCCACC   480
CTTTCGGGCA GGTCCCCGGC ATGTCAAGCC CTGGTAAGGT TCTTCGCGTT GCTTCGAATT   540
AAACCACATG CTCCACCGCT TGTGCGGGCC CCCGTCAATT CCTTTGAGTT TCAACCTTGC   600
GGCCGTACTC CCCAGGCGGG ATGCTTATTG TGTTAACTAC GGCACGGAAG AGTCCTTCTC   660
CCCCACACCT AGCATCCATC GTTTACAGCG TGGACTACCA GGGTATCTAA TCCTGTTCGC   720
TCCCCACGCT TTCGTGCCTC AGCGTCAGTT ACGGTCCAGA CGGCCGCCTT CGCCACTGGT   780
GTTCCTCCCG ATATCTACGC ATTTCACCGC TACACCGGGA ATTCCGCCGT CCTCTCCCGC   840
ACTCAAGCTA TGCAGTATTA AGCGCAATCC TTAGGTTGAG CCTAAGGCTT TCACGCTTAA   900
CTCGCATAGC CGCCTACGCA CCCTTTACGC CCAGTAATTC GGACAAACGC TCGCCACCTA   960
CGTATTACCG CGGCTGCTGG CACGTAGTTA GCCGTGGCTT TTTAAACGGG TACTATCTCC  1020
TACTTCTCCC CGTCCAAAGA GGTTTACACC CCGAAGGGCT TCTTCCCTCA CGCGGCGTCG  1080
CTGCGTCAGG CTTCCGCCCA TTGCGCAAGA TTCCCCGCTG CTGCCTCCCG TAGGAGTGTG  1140
GGCCGTGTCT CAGTCCCACT GTGGCCGTAC ACCCTCTCAG GCCGGCTACC CGTCGTCGCC  1200
TTGGTGAGCC GTTACCCCAC CAACTAGCTG ATGGGCCGCG AGCCCATCCC CAGCC       1255
```

Figure 14

**16SrDNA consensus sequence for *Caldicellulosiruptor* sp. DIB107C (SEQ ID NO. 7)**

```
GACTTCACCC CCAATCATCA GCCCCACCTT CAACACAGCT TAACCTGTGT CTTCAGGTGT      60
TGCTGACTCT CATGGTGTGA CGGGCGGTGT GTACAAGGCC CGGGAACGTA TTCACCGCGG     120
CATGCTGATC CGCGATTACT AGCGATTCCG ACTTCATGCA GGCGAGTTGC AGCCTGCAAT     180
CCGAACTGGG GGTGCTTTTT TGGGATTCGC TCCGGCTCGC GCCTTCGCAC GCCCTCTGTA     240
GCACCCATTG TAGCACGTGT GTAGCCCAGG GCATAAGGGG CATGATGATT TGACGTCATC     300
CCCACCTTCC TCCGCCTCAT CGACGGCAGT CCCCTTAGAG TGCCCACCAT TACGCGCTGG     360
CAACTAAGGG CAGGGGTTGC GCTCGTTGCG GGACTTAACC CAACATCTCA CGACACGAGC     420
TGACGACAAC CATGCACCAC CTGTGTCCGG GCTCCTGCTC TCATCGAACA GGCACCCCAC     480
CCTTTCGGGC AGGTCCCGG CATGTCAAGC CCTGGTAAGG TTCTTCGCGT TGCTTCGAAT     540
TAAACCACAT GCTCCACCGC TTGTGCGGGC CCCCGTCAAT TCCTTTGAGT TTCAACCTTG     600
CGGCCGTACT CCCCAGGCGG GATGCTTATT GTGTTAACTA CGGCACGGAG GAGTCCTTCT     660
CCCCCACACC TAGCATCCAT CGTTTACAGC GTGGACTACC AGGGTATCTA ATCCTGTTCG     720
CTCCCCACGC TTTCGTGCCT CAGCGTCAGT TACGGTCCAG ACGGCCGCCT TCGCCACTGG     780
TGTTCCTCCC GATATCTACG CATTTCACCG CTACACCGGG AATTCCGCCG TCCTCTCCCG     840
CACTCAAGCT ATGCAGTATT AAGCGCAATC CTTAGGTTGA GCCTAAGGCT TTCACGCTTA     900
ACTCGCATAG CCGCCTACGC ACCCTTTACG CCCAGTAATT CCGGACAACG CTCGCCACCT     960
ACGTATTACC GCGGCTGCTG GCACGTAGTT AGCCGTGGCT TTTTAAACGG GTACTATCTC    1020
CTACTTCTCC CCGTCCAAAG AGGTTTACAC CCCGAAGGGC TTCTTCCCTC ACGCGGCGTC    1080
GCTGCGTCAG GCTTCCGCCC ATTGCGCAAG ATTCCCGCT GCTGCCTCCC GTAGGAGTGT    1140
GGGCCGTGTC TCAGTCCCAC TGTGGCCGTA CACCCTCTCA GGCCGGCTAC CCGTCGTCGC    1200
CTTGGTGAGC CGTTACCTCA CCAACTAGCT GATGGGCCGC GAGCCCATCC CCAGCCGGAT    1260
TACTCCTTTC ACCACATCAC CATGCGATGA CGTGGTCCCA TCGGGTATTA GCAGCCCTTT    1320
CGAGCTGTTA TCCCCGTGCT GGGGTAGGT TGCTCACGTG TTACTCACCC GTCCGCCGCT    1380
AAGATGGCAG CCTCCAGCTC ATCACCTTCA ACCACCATCT CCGCTCGACT TGCATGCGTT    1420
AGGCACGCCG CCAGCGTTCG TCCTGA                                          1446
```

FIGURE 15

**16SrDNA consensus sequence for *Thermoanaerobacter* sp. DIB004G (SEQ ID NO. 8)**

```
ggntgggtca ccggcttcgg gtgncgcagg ctctcgtggt gtgacgggcg gtgtgtacaa    60
ggcccgggaa cgtattcacc gcggcatgct gatccgcgat tactagcgat tccgacttca   120
tgcaggcgag ttgcagcctg caatccgaac ttggaccggc ttttgggat tcgctccgcc   180
tcacggcttc gcttccctct gtaccggcca ttgtagcacg tgtgtggccc agggcattta   240
gggcatgatg atttgacgtc atccccacct tcctccgtgt cctccacggc agtccctcta   300
gagtgccccgg cntaccngct ggcaactaga ggcaggggtt gcgcncgttg cgggacntaa   360
cccaacatct cacgacacga gctgacgaca accatgcacc acctgtgcag gctcctnacc   420
tcccggtaag gtcgctcccc tttcggttcg ctactacctg catgtcaagc cctggtaagg   480
ttcttcgcgt tgcttcgaat taaaccacat gctccaccgc ttgtgcgggc ccccgtcaat   540
tcctttgagt ttcaaccttg cggccgtact cccaggcgg ggtacttatt gcgttcgcta   600
cggcacggaa cgcttccgcg ccccacacct agtacccatc gtttacagcg tggactacca   660
gggtatctaa tcctgttcgc tccccacgct ttcgcgcctc agcgtcaggg ccagtccaga   720
gagtcgcctt cgccactggt attcctcccg atatctacgc atttcaccgc tacaccggga   780
atnccactcc cctctcctgc cctctagcca atcagtttca gatgctaccc cccggttgag   840
cccgggtctt ttacacctga cttgattgac cgcctacgcg ccctntacgc ccagtaattc   900
cggacaacgc tcgccccta cgtcttaccg cggctgctgg cacgnagtta gccggggctt   960
tcgtgtggta ccgtcatccc ttcnccccac actaacgggg tttacaaccc gaaggccttc  1020
ctccccacg cggcgtcgct gggtcaggct tccgccatt gcccaagatt cccactgct  1080
gcctccgta ggagtctggg ccgtgtctca gtcccagtgt ggccgtccac cctctcaggc  1140
cggctaccg tgtcgcctt ggtaggccgt tnccctacca actagctgat gggacgcggg  1200
cccatcctta agcggtagct tgcgcttccc ttncctccct ataggatgcc ctataaggag  1260
ctnatccagt antaccaccc cttncgaggt gcnatcccgg tcttaagggt aggttgccca  1320
cgcgttactc acccgtccgc cgctatccgc cacccaacta cgttgagtgc cggaccgctc  1380
gactgcatgt gntaggcacg ccgccagcgt tcgtcctgag cc                    1422
```

Figure 16

**16SrDNA consensus sequence for *Thermoanaerobacter* sp. DIB087G (SEQ ID NO. 9)**

```
ACTCAAGTGG GCACGTTTTT TTCTCTTCAT CACGTTTCTA ACATGCCCAC TTGAGTGCCG      60
GGTTGGGTCA CCGGCTTCGG GTGTTGCAGA CTCTCGTGGT GTGACGGGCG GTGTGTACAA     120
GGCCCGGGAA CGTATTCACC GCGGCATGCT GATCCGCGAT TACTAGCGAT TCCGACTTCA     180
TGCAGGCGAG TTGCAGCCTG CAATCCGAAC TTGGACCGGC TTTTTGGGGT CCGCTCCAGA     240
TCGCTCCTTC GCCTCCCTCT GTACCGGCCA TTGTAGCACG TGTGTGGCCC AGGGCATATA     300
GGGCATGATG ATTTGACGTC ATCCCCACCT TCCTCCGTGT TGTCCACGGC AGTCCCTCTA     360
GAGTGCCTCC GTCACTCAAC TGAACACGCT ATCCCTTCCT CTCTACTCTT TCCTAACATG     420
TTCAGTTGAG TGACGGACTG GCAACTAGAA GCAAGGGTTG CGCTCGTTGC GGGACTTAAC     480
CCAACATCTC ACGACACGAG CTGACGACAA CCATGCACCA CCTGTGCAGG CTCCCGGCAC     540
TCAAGTAGGC ACTTCATTCT CCCTCTTACT ACCTTCTCTA TCATGCCCAC TTGAGTGCCG     600
GGTCGCTCAC CTTTCGGCTC GCTACTACCT GCATGTCAAG CCCTGGTAAG GTTCTTCGCG     660
TTGCTTCGAA TTAAACCACA TGCTCCACCG CTTGTGCGGG CCCCCGTCAA TTCCTTTGAG     720
TTTCAACCTT GCGGCCGTAC TCCCCAGGCG GGGTACTTAT TGCGTTAACT ACGGCACGGA     780
ATGCTTCCGC ATCCCACACC TAGTACCCAT CGTTTACGGC GTGGACTACC AGGGTATCTA     840
ATCCTGTTTG CTCCCCACGC TTTCGCGCCT CAGCGTCAGG GTCAGTCCAG AGAGTCGCCT     900
TCGCCACTGG TATTCCTCCC GATATCTACG CATTTCACCG CTACACCGGG AATTCCACTC     960
CCCTCTCCTG CCCTCTAGCC ACCCAGTTTC ATGTGCATCC CCGGGTTGA GCCCGGGTTT     1020
TTTACACCTG ACTTAAGTGG CCGCTACGC GCCCTTACG CCCAGTAATT CCGGACAACG     1080
CTCGCCCCCT ACGTCTTACC GCGGCTGCTG GCACGTAGTT AGCCGGGGCT TTCGTGTGGT     1140
ACCGTCATCT ATTCTTCCCA CACTATCGAG CTTTACGACC CGAAGGCCTT CTTCGCTCAC     1200
GCGGCGTCGC TGCGTCAGGC TTTCGCCCAT TGCGCAAGAT TCCCACTGC TGCCTCCCGT     1260
AGGAGTCTGG GCCGTGTCTC AGTCCCAGTG TTGGCCGACCA CCCTCTCAGG CCGGCTACCC   1320
GTCGTCGCCT TGGTAGGCCG TTACCCTACC AACTAGCTGA TGGGACGCGG GCCCATCCTT   1380
AAGCGGTAGC TTCCGCTACC TTCCCTCCTC ATAGGATGCC CTACAAGGAG CTTATCCAGT   1440
ATTAGCACCC CTTTCGAGGT GTTATCCCGG TCTTAAGGGT AGGTTGCCCA CGCGTTACTC   1500
ACCCGTCCGC CGCTATCCGG CACTCAACTC CGTGCTTACC TTACTTGCA CCACTTTTAT    1560
TACTTCTTC TTCTACTATA CTTCCTTCCC CTTAAGTAAG CACTTAGTTG AGTGCCGGAC    1620
CGCTCGACTT GCATGTGTTA GGCACGCCGC CAGCGTTCG                          1660
```

FIGURE 17

**16SrDNA consensus sequence for *Thermoanaerobacter* sp. DIB097X (SEQ ID NO. 10)**

```
CCCGGTTGGG TCACCGGCTT CGGGTGTCGC AGGCTCTCGT GGTGTGACGG GCGGTGTGTA      60
CAAGGCCCGG GAACGTATTC ACCGCGGCAT GCTGATCCGC GATTACTAGC GATTCCGACT     120
TCATGCAGGC GAGTTGCAGC CTGCAATCCG AACTTGGACC GGCTTTTTGG GATTCGCTCC     180
GCCTCGCGGC TTCGCTCCCC TCTGTACCGG CCATTGTAGC ACGTGTGTGG CCCAGGGCAT     240
ATAGGGCATG ATGATTTGAC GTCATCCCCA CCTTCCTCCG TGTCCTCCAC GGCAGTCCCC     300
CTAGAGTGCC CGGCTTACCC GCTGGCAACT AGAGGCAGGG GTTGCGCTCG TTGCGGGACT     360
TAACCCAACA TCTCACGACA CGAGCTGACG ACAACCATGC ACCACCTGTG CAGGCTCCTT     420
ACCTCCCGGT AAGGTCGCTC CCCTTTCGGT TCGCTACTAC CTGCATGTCA AGCCCTGGTA     480
AGGTTCTTCG CGTTGCTTCG AATTAAACCA CATGCTCCAC CGCTTGTGCG GGCCCCCGTC     540
AATTCCTTTG AGTTCAACC  TTGCGGCCGT ACTCCCCAGG CGGGGTACTT ATTGCGTTCG     600
CTACGGCACG GAACGCTTCC GCGCCCCACA CCTAGTACCC ATCGTTTACA GCGTGGACTA     660
CCAGGGTATC TAATCCTGTT CGCTCCCCAC GCTTTCGCGC CTCAGCGTCA GGGCCAGTCC     720
AGAGAGTCGC CTTCGCCACT GGTATTCCTC CCGATATCTA CGCATTTCAC CGCTACACCG     780
GGAATTCCAC TCCCCTCTCC TGCCCTCTAG CCAATCAGTT TCAGATGCTA CCCCCGGGTT     840
CAGCCCCGCT CTTTTACACC TGACTTGATT GACCCCCTAC GCCCCCTTTA CCCCCAGTAA     900
TTCCGGACAA CGCTCGCCCC CTACGTCTTA CCGCGGCTGC TGGCACGTAG TTAGCCGGGG     960
CTTTCGTGTG GTACCGTCAT CCCTTCTTCC CACACTAACG GCTTTACAA  CCCGAAGCCC    1020
TTCCTCCCCC ACGCGGCGTC GCTGGGTCAG GCTTCCGCCC ATTGCCCAAG ATTCCCCACT    1080
CCTGCCTCCC GTACGAGTCT GCGCCCTGTC TCAGTCCCAG TGTGGCCCAC CACCCTCTCA    1140
GGCCGGCTAC CCGTCGTCGC CTTGGTAGGC CGTTACCCTA CCAACTAGCT GATGGGACGC    1200
GGGCCCATCC TTAAGCGGTA GCTTGCGCCT CCCTTTCCTC CCTATAGGAT GCCCTATAAG    1260
GAGCTTATCC AGTATTACCA CCCCTTTCGA GGTGCTATCC CGGTCTTAAG GGTAGGTTGC    1320
CCACGCGTTA CTCACCCGTC CGCCGCTATC CGCCACCCAA CTACGTTGAG TGCCCGACCG    1380
CTCGACTTGC ATGTGTTAGG CACGCCGCCA GCGTTCGTCC TGAGCCATGA TCAAAC        1436
```

FIGURE 18

**16SrDNA consensus sequence for *Thermoanaerobacter* sp. DIB101G (SEQ ID NO. 11)**

```
gctcaggacg aacgctggcg gcgtgcctaa cacatgcaag tcgagcggtc cggcactcaa      60
ctaagtgctt acttaagggg aaggaagtat agtagaagaa gaaggtaata aaagtgatgc     120
aaagtaaggt aagcacggag ttgagtgccg gatagcggcg gacgggtgag taacgcgtgg     180
gcaacctacc cttaagaccg ggataacacc tcgaaagggg tgctaatact ggataagctc     240
cttgtagggc atcctatgag cagggaaggt agcggaagct accgcttaag gatgggcccg     300
cgtcccatca gctagttggt agggtaacgg cctaccaagg cgacgacggg tagccggcct     360
gagagggtgg tcggccacac tgggactgag acacggccca gactcctacg ggaggcagca     420
gtggggaatc ttgcgcaatg gcgaaagcc tgacgcagcg acgccgcgtg agcgaagaag     480
gccttcgggt cgtaaagctc gatagtgtgg gaagaataga tgacggtacc acacgaaagc     540
cccggctaac tacgtgccag cagccgcggt aagacgtagg gggcgagcgt tgtccggaat     600
tactgggcgt aaagggcgcg taggcggcca cttaagtcag gtgtaaaaaa cccgggctca     660
acccggggga tgcacatgaa actgggtggc tagagggcag gagaggggag tggaattccc     720
ggtgtagcgg tgaaatgcgt agatatcggg aggaatacca gtggcgaagg cgactctctg     780
gactgaccct gacgctgagg cgcgaaagcg tggggagcaa acaggattag ataccctggt     840
agtccacgcc gtaaacgatg ggtactaggt gtcggatgcg gaagcattcc gtgccgtagt     900
taacgcaata agtacccgc ctggggagta cggccgcaag gttgaaactc aaaggaattg     960
acgggggccc gcacaagcgg tggagcatgt ggtttaattc gaagcaacgc gaagaacctt    1020
accagggctt gacatgcagg tagtagcgag ccgaaaggtg agcgacccgg cactcaagtg    1080
```

FIGURE 19

**16SrDNA consensus sequence for *Thermoanaerobacter* sp. DIB101X (SEQ ID NO. 12)**

```
GCCCCACTTT CGACGGCTCC CTCCTTCCCG GTTGGGTCAC CGGCTTCGGG TGTCGCAGGC    60
TCTCGTGGTG TGACGGGCGG TGTGTACAAG GCCCGGGAAC GTATTCACCG CGGCATGCTG   120
ATCCGCGATT ACTAGCGATT CCGACTTCAT GCAGGCGAGT TGCAGCCTGC AATCCGAACT   180
TGGACCGGCT TTTTGGGATT CGCTCCGCCT CGCGGCTTCG CTTCCCTCTG TACCGGCCAT   240
TGTAGCACGT GTGTGGCCCA GGGCATATAG GGCATGATGA TTTGACGTCA TCCCCACCTT   300
CCTCCGTGTC CTCCACGGCA GTCCCTCTAG AGTGCCCGGC TTACCCGCTG GCAACTAGAG   360
GCAGGGGTTG CGCTCGTTGC GGGACTTAAC CCAACATCTC ACGACACGAG CTGACGACAA   420
CCATGCACCA CCTGTGCAGG CTCCTTACCT CCCGGTAAGG TCGCTCCCCT TTCGGTTCGC   480
TACTACCTGC ATGTCAAGCC CTGGTAAGGT TCTTCGCGTT GCTTCGAATT AAACCACATG   540
CTCCACCGCT TGTGCGGGCC CCCGTCAATT CCTTTGAGTT TCAACCTTGC GGCCGTACTC   600
CCCAGCCGGC GTACTTATTG CGTTCGCTAC GGCACGGAAC GCTTCCGCCC CCCACACCTA   660
GTACCCATCG TTTACAGCGT GGACTACCAG GGTATCTAAT CCTGTTCGCT CCCCACGCTT   720
TCGCGCCTCA GCGTCAGGGC CAGTCCAGAG AGTCGCCTTC GCCACTGGTA TTCCTCCCGA   780
TATCTACGCA TTTCACCGCT ACACCGGGAA TTCCACTCCC CTCTCCTGCC CTCTAGCCAA   840
TCAGTTTCAG ATGCTACCCC CGGGTTGAGC CCGGGTCTTT TACACCTGAC TTGATTGACC   900
GCCTACGCGC CCTTTACGCC CAGTAATTCC GGACAACGCT CGCCCCCTAC GTCTTACCGC   960
GGCTGCTGGC ACGTAGTTAG CCGGGGCTTT CGTGTGGTAC CGTCATCCCT TCTTCCCACA  1020
CTAACGGGGT TTACAACCCG AAGGCCTTCC TCCCCCACGC GGCGTCGCTG GGTCAGGCTT  1080
CCGCCCATTG CCCAAGATTC CCCACTGCTG CCTCCGTGAG GAGTCTGGGC CGTGTCTCAG  1140
TCCCAGTGTG CCCGACCACC CTCTCAGGCC GGCTACCCCT CCTCCCCTTC GTAGCCCGTT  1200
ACCCTACCAA CTAGCTGATG GGACGCGGGC CCATCCTTAA GCGGTAGCTT GCGCCTCCCT  1260
TTCCTCCCTA TAGGATGCCC TATAAGGAGC TTATCCAGTA TTACCACCCC TTTCGAGGTG  1320
CTATCCCGGT CTTAAGGGTA GGTTGCCCAC GCGTTACTCA CCCGTCCGCC GCTATCCGCC  1380
ACCCAACTAC GTTGAGTGCC GGACCGCTCG ACTTCCATCT GTTACCCACC CCCCCACCCT  1440
TCGTCCTGAG C                                                      1451
```

Figure 20

**16SrDNA consensus sequence for *Thermoanaerobacter* sp. DIB103X (SEQ ID NO. 13)**

```
TTCACCCCAA TCACCTGCCC CACCTTCGAC GGCTCCCTCC TCCCGGTTG GGTCACCGGC      60
TTCGGGTGTC GCAGGCTCTC GTGGTGTGAC GGGCGGTGTG TACAAGGCCC GGGAACGTAT    120
TCACCGCGCC ATCCTCATCC CCGATTACTA CCCATTCCGA CTTCATCCAC CCCAGTTGCA    180
GCCTGCAATC CGAACTTGGA CCGGCTTTTT GGGATTCGCT CCGCCTCGCG GCTTCGCTCC    240
CCTCTGTACC GGCCATTGTA GCACGTGTGT GGCCCAGGGC ATATAGGGCA TGATGATTTG    300
ACGTCATCCC CACCTTCCTC CGTGTCCTCC ACGGCAGTCC CCCTAGAGTG CCCGGCTTAC    360
CCGCTGGCAA CTAGAGGCAG GGGTTGCGCT CGTTGCGGGA CTTAACCCAA CATCTCACGA    420
CACGAGCTGA CGACAACCAT GCACCACCTG TGCAGGCTCC TTACCTCCCG GTAAGGTCGC    480
TCCCCTTTCG GTTCGCTACT ACCTGCATGT CAAGCCCTGG TAAGGTTCTT CGCGTTGCTT    540
CGAATTAAAC CACATGCTCC ACCGCTTGTG CGGGCCCCCG TCAATTCCTT TGAGTTTCAA    600
CCTTGCGGCC GTACTCCCCA GGCGGGGTAC TTATTGCGTT CGCTACGGCA CGGAACGCTT    660
CCGCGCCCCA CACCTAGTAC CCATCGTTTA CAGCGTGGAC TACCAGGGTA TCTAATCCTG    720
TTCGCTCCCC ACGCTTTCGC GCCTCAGCGT CAGGGCCAGT CCAGAGAGTC GCCTTCGCCA    780
CTGGTATTCC TCCCGATATC TACGCATTTC ACCGCTACAC CGGGAATTCC ACTCCCCTCT    840
CCTGCCCTCT AGCCAATCAG TTTCAGATGC TACCCCCGGG TTGAGCCCGG GTCTTTTACA    900
CCTGACTTGA TTGACCGCCT ACGCGCCCTT TACGCCCAGT AATTCCGGAC AACGCTCGCC    960
CCCTACGTCT TACCGCGGCT GCTGGCACGT AGTTAGCCGG GGCTTTCGTG TGGTACCGTC   1020
ATCCCTTCTT CCCACACTAA CGGGGTTTAC AACCCGAAGG CCTTCCTCCC CCACGCGGCG   1080
TCGCTGGGTC AGGCTTCCGC CCATTGCCCA AGATTCCCCA CTGCTGCCTC CCGTAGGAGT   1140
CTGGGCCGTG TCTCAGTCCC AGTGTGGCCG ACCACCCTCT CAGGCCGGCT ACCCGTCGTC   1200
GCCTTGGTAG GCCGTTACCC TACCAACTAG CTGATGGGAC GCGGGCCCAT CCTTAAGCGG   1260
TAGCTTGCGC CTCCCTTTCC TCCCTATACG ATCCCCTATA AGCACCTTAT CCACTATTAC   1320
CACCCCTTTC GAGGTGCTAT CCGGTCTTA AGGGTAGGTT GCCCACGCGT TACTCACCCG   1480
TCCGCCGCTA TCCGCCACCC AACTACGTTG AGTGCGGGAC CGCTCGACTT GCATGTGTTA   1540
GGCACGCCGC CAGCGTTCGT CCTGA                                        1565
```

Figure 21

**16SrDNA consensus sequence for *Thermoanaerobacter* sp. DIB104X (SEQ ID NO. 14)**

```
ACTCAAGTGG GCACGTTTTT TTCTCTTCAT CACGTTTCTA ACATGCCCAC TTGAGTGCCG    60
GGTTGGGTCA CCGGCTTCGG GTGTTGCAGA CICTCGTGGT GTGACGGGCG GTGTGTACAA   120
GGCCCGGGAA CGTATTCACC GCGGCATGCT GATCCGCGAT TACTAGCGAT TCCGACTTCA   180
TGCAGGCGAG TTGCAGCCTG CAATCCGAAC TGGACCGGC TTTTTGGGGT CCGCTCCAGA   240
TCGCTCCTTC GCCTCCCTCT GTACCGGCCA TIGTAGCACG TGTGTGGCCC AGGGCATATA   300
GGGCATGAIG ATTTGACGTC ATCCCCACCT TCCTCCGTGT TGTCCACGGC AGTCCCTCTA   360
GAGTGCCTCC GTCACTCAAC TGAACACGCT ATCCCTTCCT CTCTACTCTT TCCTAACATG   420
TTCAGTTGAG TGACGGACTG GCAACTAGAA GCAAGGGTTG CGCTCGTTGC GGGACTTAAC   480
CCAACATCTC ACGACACGAG CTGACGACAA CCATGCACCA CCTGTGCAGG CTCCCGGCAC   540
TCAAGTAGGC ACTTCATTCT CCCTCTTACT ACCTTCTCTA TCATGCCCAC TTGAGTGCCG   600
GGTCGCTCAC CTTTCGGCTC GCTACTACCT GCATGTCAAG CCCIGGTAAG GTTCTTCGCG   660
TTGCTTCGAA TTAAACCACA TGCTCCACCG CTTGTGCGGG CCCCCGTCAA TTCCTTTGAG   720
TTTCAACCTT GCGGCCGTAC TCCCCAGGCG GGGTACTTAT TGCGTTAACT ACGGCACGGA   780
ATGCTTCCGC ATCCCACACC TAGTACCCAT CGTTTACGGC GTGGACTACC AGGGTATCTA   840
ATCCTGTTTG CTCCCCACGC TTTCGCGCCT CAGCGTCAGG GTCAGTCCAG AGAGTCGCCT   900
TCGCCACTGG TATTCCTCCC GATATCTACG CATTTCACCG CTACACCGGG AATTCCACTC   960
CCCTCTCCTG CCCTCTAGCC ACCCAGTTTC AIGTGCATCC CCCGGGTTGA GCCCGGGTTT  1020
TTTACACCTG ACTTAAGTGG CCGCCTACGC GCCCTTTACG CCCAGTAATT CCGGACAACG  1080
CTCGCCCCCT ACGTCTTACC GCGGCTGCTG GCACGTAGTT AGCCGGGGCT TTCGTGTGGT  1140
ACCGTCATCT ATTCTTCCCA CACTATCGAC CTTACGACC CCAAGCCCTT CTTCGCTCAC  1200
GCGGCGTCGC TGCGTCAGGC TTTCGCCCAT TGCGCAAGAT TCCCCACTGC TGCCTCCCGT  1260
AGGAGTCTGG GCCGTGTCTC AGTCCCAGTG TGGCCGACCA CCCTCTCAGG CCGGCTACCC  1320
GTCGTCGCCT TGGTAGGCCG TTACCCTACC AACTAGCTGA TGGACGCGG GCCCATCCTT  1380
AAGCGCTACC TTCCCCTACC TTCCCTCCTC AIAGCATCCC CTACAAGCAC CTTATCCAGT  1440
ATTAGCACCC CTTTCGAGGT GTTATCCCGG TCTTAAGGGT AGGITGCCCA CGCGTTACTC  1500
ACCCGTCCGC CGCTATCCGG CACTCAACTC CGTGCTTACC TTACTTTGCA CCACTTTTAT  1560
TACTTTCTTC TTCTACTATA CTTCCTTCCC CTTAAGTAAG CACTTAGTTG AGTGCCGGAC  1620
CGCTCGACTT GCATGTGTTA GGCACGCCGC CAGCGTTCGT CCTGA                  1665
```

Figure 22

**16SrDNA consensus sequence for *Thermoanaerobacter* sp. DIB107X (SEQ ID NO. 15)**

```
TCAGGACGAA CGCTGGCGGC GTGCCTAACA CATGCAAGTC GAGCGGTCCG GCACTCAACG      60
TAGTTGAGTG GCGGATAGCG GCGGACGGGT GAGTAACGCG TGGGCAACCT ACCCTTAAGA     120
CCGGGATAGC ACCTCGAAAG GGGTGGTAAT ACTGGATAAG CTCCTTATAG GGCATCCTAT     180
AGGGAGGAAA GGGAAGCGCA AGCTACCGCT TAAGGATGGG CCCGCGTCCC ATCAGCTAGT     240
TGGTAGGGTA ACGGCCTACC AAGGCKACGA CGGGTAGCCG GCCTGAGAGG GTGGTCGGCC     300
ACACTGGGAC TGAGACACGG CCCAGACTCC TACGGGAGGC AGCAGTGGGG AATCTTGGGC     360
AATGGGCGGA AGCCTGACCC AGCGACGCCG CGTGGGGGAG GAAGGCCTTC GGGTTGTAAA     420
CCCCGTTACT GTGGGAACAA GCCATGACGG TACCACACCA AAGCCCCGCC TAACTACGTG     480
CCAGCAGCCG CGGTAAGACG TAGGGGGCGA GCGTTGTCCG GAATTACTGG GCGTAAAGGG     540
CGCGTAGGCG GTCAATCAAG TCAGGTGTAA AAGACCCGGG CTCAACCCGG GGGTAGCACC     600
TGAAACTGGT TGGCTAGAGG GCAGGAGAGG GGAGTGGAAT TCCGGTGTA GCGGTGAAAT      660
GCGTAGATAT CGGGAGGAAT ACCAGTGGCG AAGGCGACTC TCTGGACTGG CCCTGACGCT     720
GAGGCGCGAA AGCGTGGGGA GCGAACAGGA TTAGATACCC TGGTAGTCCA CGCTGTAAAC     780
GATGGGTACT AGGTGTGGGG CGCGGAAGCG TTCCGTGCCG TAGCGAACGC AATAAGTACC     840
CCGCCTGGGG AGTACGGCCG CAACGTTGAA ACTCAAAGGA ATTCACGGGG CCCCCCACAA     900
GCGGTGGAGC ATGTGGTTTA ATTCGAAGCA ACGCGAAGAA CCTTACCAGG GCTTGACATG     960
CAGGTGGTAG CGAACCGAAA GGTGAGCGAC CTTACCGGGA GGTAAGGAGC CTGCACAGGT    1020
GGTGCATGGT TGTCGTCAGC TCGTGTCGTG AGATGTTGGG TTAAGTCCCG CAACGAGCGC    1080
AACCCCTGCC TCTAGTTGCC AGCGG                                         1105
```

METHODS AND MICROBIAL CULTURES FOR IMPROVED CONVERSION OF LIGNOCELLULOSIC BIOMASS

CROSS-REFERENCE TO RELATED APPLICATIONS

This application is a U.S. National stage of PCT/EP2013/064256 filed on Jul. 5, 2013, which claims priority from U.S. Provisional Application Ser. No. 61/669,963 filed on Jul. 10, 2012 and EP Application Serial No. 12175673.8 filed on Jul. 10, 2012, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCT_EP2013_064256_SEQID" created on 30 Dec. 2014 and having a size of 30 Kilobytes. The sequence listing contained in this ASCII formatted document forms part of the specification and is herein incorporated by reference in its entirety.

FIELD OF THE DISCLOSURE

The present disclosure pertains to methods and microbial cultures for converting lignocellulosic biomass to biofuels and/or other carbon-based chemicals.

BACKGROUND

In general, fermentation products are produced by degradation of starch-containing material into fermentable sugars by liquefaction and saccharification followed by conversion of the sugars directly or indirectly into the desired fermentation product using a fermenting organism.

However, the industrial production of fermentation products such as ethanol and lactic acid is facing the challenge of redirecting the production process from fermentation of relatively easily convertible but expensive starchy materials, to the complex but inexpensive lignocellulosic biomass such as plant biomass.

Unlike starch, which contains homogenous and easily hydrolyzed polymers, lignocellulosic biomass contains variable amounts of cellulose, hemicellulose, lignin and small amounts of protein, pectin, wax and other organic compounds. Cellulosic biomass is a vast poorly exploited resource, and in some cases a waste problem. However, hexoses from cellulose can be converted by yeast to fuel ethanol for which there is a growing demand. Pentoses from hemicellulose cannot yet be converted to ethanol commercially but several promising ethanologenic microorganisms with the capacity to convert pentoses and hexoses are under development.

Typically, the first step in utilization of lignocellulosic biomass is a pre-treatment step, in order to fractionate the components of lignocellulosic material and increase their surface area. The pre-treatment method most often used is acid hydrolysis, where the lignocellulosic material is subjected to an acid such as sulphuric acid whereby the sugar polymers cellulose and hemicellulose are partly or completely hydrolysed to their constituent sugar monomers and the structure of the biomass is destroyed facilitating access of hydrolytic enzymes in subsequent processing steps.

Another type of lignocellulose hydrolysis is steam explosion, a process comprising heating of the lignocellulosic material by steam injection to a temperature of 190-230° C. A further method is wet oxidation wherein the material is treated with oxygen at 150-185° C. The pre-treatments can be followed by enzymatic hydrolysis to complete the release of sugar monomers. This pre-treatment step results in the hydrolysis of cellulose into glucose while hemicellulose is partially or completely transformed into the pentoses xylose and arabinose and the hexoses glucose, mannose and galactose. Thus, in contrast to starch, the hydrolysis of lignocellulosic biomass results in the release of pentose sugars in addition to hexose sugars. This implies that useful fermenting organisms need to be able to convert both hexose and pentose sugars to desired fermentation products such as ethanol.

After the pre-treatment, the lignocellulosic biomass processing schemes involving enzymatic or microbial hydrolysis commonly involve five biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g. glucose, mannose, and galactose); (4) the fermentation of pentose sugars (e.g., xylose and arabinose) and (5) the conversion of sugar alcohols like sorbitol, mannitol or xylitol.

Each processing step can make the overall process more costly and, therefore, decreases the economic feasibility of producing biofuel or carbon-based chemicals from cellulosic biological material. Thus, there is a need to develop methods that reduce the number of processing steps needed to convert cellulosic biological material to biofuel and other commercially desirable materials.

The five biologically mediated transformations may occur in a single step in a process configuration called consolidated bioprocessing (CBP), which is distinguished from other less highly integrated configurations in that CBP does not involve a dedicated process step for cellulase and/or hemicellulase production. CBP offers the potential for higher efficiency than processes requiring dedicated cellulase production.

Current CBP processes include extensive and costly pretreatment of the material by mechanical, thermochemical, and biochemical processes. Generally, the goals of such pretreatment processes include (1) rendering the cellulosic and hemicellulosic polymers more accessible to microorganisms, and (2) converting the complex cellulosic and hemicellulosic polysaccharides into simpler, fermentable sugars or other simple compounds, that are more readily converted into fuels and other chemicals by microorganisms. The mechanical, thermochemical, and biochemical processes frequently used in the pretreatment of lignocellulosic material constitute a major cost and are not completely effective.

Furthermore, the microorganisms currently used for the production of fuels and other chemicals from lignocellulosic material lack the necessary cellular machinery for both breaking down the complex plant polysaccharides into sugars (saccharification) and then converting the various resulting sugars into fuels and other chemical products in an efficient manner.

Ideally, desirable characteristics of different microorganisms could be utilized simultaneously by fermenting lignocellulosic biomass with co-cultures of the microorganisms. However, the optimal conditions for fermentation of lignocellulosic biomass vary greatly from species to species.

Under the most favorable conditions, monocultures of bacteria can replicate very quickly and efficiently produce the desired fermentation product. However, due to evolutionary pressure, when a co-culture of microorganisms is present, the species that can grow the fastest often dominates. Many variables influence the success of bacterial fermentation of lignocellulosic biomass, including but not limited to: temperature, pH, growth medium, and pre-treatment protocol. Identifying the small window of conditions suitable for co-culturing at least two microorganisms, while the organisms simultaneously ferment lignocellulosic biomass, presents a significant challenge.

Thus, there remains a substantial unmet need for bioconversion processes that take advantage of better microorganisms and/or combinations of microorganisms in order to convert a broader spectrum of lignocellulosic biomass and saccharify complex polysaccharides to fermentable sugars for fermenting fuels and other chemicals.

Therefore, the availability of novel microorganisms and/or combinations of microorganisms for converting lignocellulosic biomass to high levels of carbon-based chemicals would be advantageous.

SUMMARY OF THE DISCLOSURE

The present disclosure relates to novel microbial co-cultures and methods using these co-cultures for the production of biofuels and/or other carbon-based chemicals.

In a first aspect, the disclosure relates to methods for producing a biofuel and/or another carbon-based chemical comprising:
a) Providing a lignocellulosic biomass
b) Contacting the lignocellulosic biomass with a first microorganism belonging to the genus *Caldicellulosiruptor*, wherein the first microorganism converts at least a portion of the biomass into mono-, di-, and/or polysaccharides; and
c) Contacting the lignocellulosic biomass with a second microorganism belonging to the genus *Thermoanaerobacter*, wherein the second microorganism converts at least a portion of the mono-, di-, and/or polysaccharides to a biofuel and/or another carbon-based product.

In a second aspect, the disclosure pertains to microbial cultures suitable for converting lignocellulosic biomass to a biofuel and/or another carbon-based chemical comprising a first microorganism belonging to the genus *Caldicellulosiruptor* and a second microorganism belonging to the genus *Thermoanaerobacter*.

In a third aspect, the disclosure pertains to methods for converting lignocellulosic biomass to a biofuel or other carbon-based product, comprising the step of contacting lignocellulosic biomass with a microbial culture according to the present disclosure for a period of time at an initial temperature and an initial pH, thereby producing an amount of a biofuel and/or other carbon-based chemicals.

In still another aspect, embodiments of this disclosure relate to methods of producing lactic acid and/or ethanol from lignocellulosic biomass, wherein the method comprises contacting the microorganisms or the microbial culture according to the present disclosure and the biomass in a medium; and fermenting the biomass under conditions and for a time sufficient to produce lactic acid, a salt or a ester thereof, and/or ethanol, in a single step process as part of a consolidated bioprocessing (CBP) system, with a cell, strain, microbial culture and/or a microorganism according to the present disclosure under suitable conditions.

Some embodiments of the present disclosure related to processes for producing a biofuel such as ethanol and/or other carbon-based chemicals. In one embodiment, the process comprises subjecting biomass which includes cellulose and hemi-cellulose containing plant materials to fermentation under thermophilic conditions in the presence of co-cultures of novel isolated cellulolytic thermophilic bacterial cells belonging to the genus *Caldicellulosiruptor* and novel isolated saccharolytic and/or xylanolytic thermophilic bacterial cells belonging to the genus *Thermoanaerobacter*.

Accordingly, the present disclosure pertains to the use of microbial strains selected from the group consisting of *Caldicellulosiruptor* sp. DIB004C (DSMZ accession number 25177), *Caldicellulosiruptor* sp. DIB101C (DSMZ accession number 25178), *Caldicellulosiruptor* sp. DIB041C (DSMZ accession number 25771), *Caldicellulosiruptor* sp. DIB087C (DSMZ accession number 25772), *Caldicellulosiruptor* sp. DIB103C (DSMZ accession number 25773), *Caldicellulosiruptor* sp. DIB104C (DSMZ accession number 25774) and *Caldicellulosiruptor* sp. DIB107C (DSMZ accession number 25775), *Thermoanaerobacter* sp. DIB004G (DSMZ accession number 25179), *Thermoanaerobacter* sp. DIB101G (DSMZ accession number 25180), *Thermoanaerobacter* sp. DIB101X (DSMZ accession number 25181), *Thermoanaerobacter* sp. DIB97X (DSMZ accession number 25308), *Thermoanaerobacter* sp. DIB87G (DSMZ accession number 25777), *Thermoanaerobacter* sp. DIB103X (DSMZ accession number 25776), *Thermoanaerobacter* sp. DIB104X (DSMZ accession number 25778), *Thermoanaerobacter* sp. DIB107X (DSMZ accession number 25779) as well as any combination of said strains and any homologs thereof for the production of biofuels and/or other carbon-based chemicals.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications cited herein.

BRIEF DESCRIPTION OF THE DRAWINGS

FIG. 8 shows a 16S rDNA from *Caldicellulosiruptor* sp. DIB004C cell (SEQ ID NO. 1)

FIG. 9 shows a 16S rDNA from *Caldicellulosiruptor* sp. DIB041C cell (SEQ ID NO. 2)

FIG. 10 shows a 16S rDNA from *Caldicellulosiruptor* sp. DIB087C cell (SEQ ID NO. 3)

FIG. 11 shows a 16S rDNA from *Caldicellulosiruptor* sp. DIB101C cell (SEQ ID NO. 4)

FIG. 12 shows a 16S rDNA from *Caldicellulosiruptor* sp. DIB103C cell (SEQ ID NO. 5)

FIG. 13 shows a 16S rDNA from *Caldicellulosiruptor* sp. DIB104C cell (SEQ ID NO. 6)

FIG. 14 shows a 16S rDNA from *Caldicellulosiruptor* sp. DIB107C cell (SEQ ID NO. 7)

FIG. 15 shows a 16S rDNA from *Thermoanaerobacter* sp. DIB004G cell (SEQ ID NO. 8)

FIG. 16 shows a 16S rDNA from *Thermoanaerobacter* sp. DIB087G cell (SEQ ID NO. 9)

FIG. 17 shows a 16S rDNA from *Thermoanaerobacter* sp. DIB097X cell (SEQ ID NO. 10)

FIG. 18 shows a 16S rDNA from *Thermoanaerobacter* sp. DIB101G cell (SEQ ID NO. 11)

FIG. 19 shows a 16S rDNA from *Thermoanaerobacter* sp. DIB101X cell (SEQ ID NO. 12)

FIG. 20 shows a 16S rDNA from *Thermoanaerobacter* sp. DIB103X cell (SEQ ID NO. 13)

FIG. 21 shows a 16S rDNA from *Thermoanaerobacter* sp. DIB104X cell (SEQ ID NO. 14)

FIG. 22 shows a 16S rDNA from *Thermoanaerobacter* sp. DIB107X cell (SEQ ID NO. 15)

DETAILED DESCRIPTION OF THE DISCLOSURE

Figure 1:
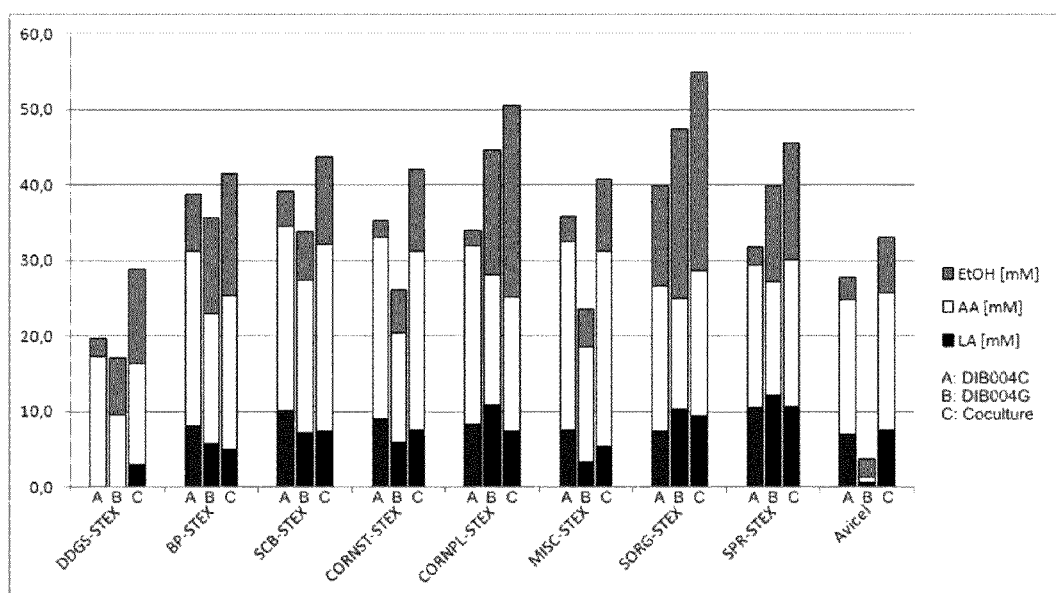
FIG. 1 shows a bar graph displaying product formation of the strains *Caldicellulosiruptor* sp. DIB004C (A) and *Thermoanaerobacter* sp. DIB004G (B) alone or in co-culture of both strains (C) for various technical substrates.

Aspects of the present disclosure relate to novel consolidated bioprocessing (CBP) methods by which the efficiency of the production of biofuels and/or other carbon-based chemicals from cellulosic biomass-containing materials can be increased. In particular, the present disclosure provides numerous microbiological co-cultures for increasing the efficiency of ethanol and/or lactic acid production from biomass.

The present disclosure relates to methods, microorganisms and microbial co-cultures useful for processing lignocellulosic biomass. The disclosure relates, in certain aspects, to microorganisms which are able to convert lignocellulosic biomass such as, for example, poplar wood chips or grass like *miscanthus*, to an economically desirable product such as, for example, a biofuel (e.g., an alcohol and/or hydrogen gas (H2)), polymer, and/or commodity carbon-based chemical like lactic acid.

Furthermore, the present disclosure relates to methods, microorganisms, and compositions useful for converting sugars like poly-, oligo, di- and/or mono-saccharides, in particular di- and/or mono-saccharides of hexoses and/or poly-, oligo, di- and/or monosaccharides of pentoses to produce carbon based chemicals like ethanol and/or lactic acid.

One aspect of the disclosure relates to methods for the conversion of lignocellulosic biomass into biofuel and/or another carbon based chemical utilizing co-cultures of at least two extremely thermophilic microorganisms, a first microorganism belonging to the genus *Caldicellulosiruptor* and a second microorganism belonging to the genus *Thermoanaerobacter*.

The term "co-culture" and/or "microbial culture" as used in the present disclosure is a mixture of at least two different microorganisms (a first and a second microorganism) that have been reproduced in predetermined culture media under controlled laboratory conditions, either together or separately. Further the term "co-culture" means a mixture of at least two different microorganisms, wherein the microorganisms are first mixes within the reaction container e.g. the container for converting the biomass to carbon-based chemicals like ethanol and/or lactic acid. The co-culture can be added to the biomass simultaneously, independently and/or with a time shift between the addition of the first microorganism and the second microorganism.

The term "xylanolytic" is intended to include the ability to hydrolyze glycosidic linkages in oligopentoses and polypentoses. The term "cellulolytic" is intended to include the ability to hydrolyze partially, substantially or completely cellulose or any of its constituents. Cellulolytic activity may also include the ability to depolymerize or debranch cellulose and hemicellulose.

By "extremely thermophilic" is meant an organism capable of growing at a temperature of 70° C. or higher. By "mesophilic" is meant an organism that thrives at a temperature of about 20° C.-45° C.

The terms "lignocellulosic biomass" and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants, and sugar-processing residues. In particular, the term "lignocellulosic biomass" according to the present disclosure should be also understood in its broadest sense, so that it apart from wood, agricultural residues, energy crops also comprises different types of waste from both industry and households. It may be any biomass containing cellulose and/or hemicellulose including grass, switchgrass, cord grass, rye grass, reed canary grass, mixed prairie grass, *miscanthus*, sugar-methoding residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, and softwood, pressmud from sugar beet, cotton stalk, banana leaves, palm oil processing residues and lignocellulosic biomass material obtained through processing of food plants. In advantageous embodiments, the lignocellulosic biomass material is grass and/or hardwood, preferably *miscanthus* grass and/or poplar wood. In particular, it is intended to designate an untreated lignocellulosic biomass and/or a lignocellulosic biomass which has been subjected to a pre-treatment step whereby e.g. lignocellulosic material has been at least partially separated into cellulose, hemicellulose and lignin thereby having increased the surface area of the material.

As used herein "efficient" growth refers to growth in which cells may be cultivated to a specified density within a specified time.

Cellobiose is a disaccharide derived from the condensation of two glucose molecules linked in a β(1→4) bond. It can be hydrolyzed to give glucose. Cellobiose has eight free alcohol (OH) groups, one either linkage and two hemiacetal linkages, which give rise to strong inter- and intra-molecular hydrogen bonds. It is a type of dietary carbohydrate also found in mushrooms.

The term "organic acid" is art-recognized. The term "lactic acid" refers to the organic acid 2-hydroxypropionic acid in either the free acid form, the salt form as well as to its esters or anhydrides. The salt form of lactic acid is "lactate" regardless of the neutralizing agent, i.e., calcium carbonate or ammonium hydroxide.

The term "acetic acid" refers to the organic acid methanecarboxylic acid, also known as ethanoic acid, in either free acid or salt form. The salt form of acetic acid is referred to as "acetate."

A strain, cell or microorganism "homolog" as used herein is considered any microorganisms that is not significantly different by means of DNA homology as defined above and exhibits the same or comparable physiological properties as described in the examples herein.

The term "mutant" as used herein refers to a bacterial cell in which the genome, including one or more chromosomes or potential extra-chromosomal DNA, has been altered at one or more positions, or in which DNA has been added or removed.

The term "progeny" is refers to a product of bacterial reproduction, a new organism produced by one or more parents.

The term "DNA-DNA relatedness" in particularly refers to the percentage similarity of the genomic or entire DNA of two microorganisms as measured by the DNA-DNA hybridization/renaturation assay according to De Ley et al. (1970) Eur. J. Biochem. 12, 133-142 or Huβ et al. (1983) Syst. Appl. Microbiol. 4, 184-192. In particular, the DNA-DNA hybridization assay preferably is performed by the DSMZ (Deutsche Sammlung von Mikroorganismen and Zellkulturen GmbH, Braunschweig, Germany) Identification Service.

The term "16S rDNA gene sequence similarity" in particular refers to the percentage of identical nucleotides between a region of the nucleic acid sequence of the 16S ribosomal RNA (rDNA) gene of a first microorganism and the corresponding region of the nucleic acid sequence of the 16S rDNA gene of a second microorganism. Preferably, the region comprises at least 100 consecutive nucleotides, more preferably at least 200 consecutive nucleotides, at least 300 consecutive nucleotides or at least 400 consecutive nucleotides, most preferably about 480 consecutive nucleotides.

The term "a microorganism" as used herein may refer to only one unicellular organism as well as to numerous single unicellular organisms. For example, the term "a microorganism of the genus *Caldicellulosiruptor*" may refer to one single *Caldicellulosiruptor* bacterial cell of the genus *Caldicellulosiruptor* as well as to multiple bacterial cells of the genus *Caldicellulosiruptor*. For example, the term "a microorganism of the genus *Thermoanaerobacter*" may refer to one single *Thermoanaerobacter* bacterial cell of the genus *Thermoanaerobacter* as well as to multiple bacterial cells of the genus *Thermoanaerobacter*. In general, the term "a microorganism" refers to numerous cells. In particular, said term refers to at least $10^3$ cells, preferably at least $10^4$ cells, at least $10^5$ or at least $10^6$ cells.

By exploiting certain desirable characteristics from each organism in the microbial culture according to the present disclosure, unexpectedly high levels of e.g. ethanol and/or lactic acid are produced in comparison to the levels of ethanol and/or lactic acid produced in monocultures of the individual microorganisms. A first microorganism capable of utilizing cellulose and hemicellulose (cellulolytic and saccharolytic) is combined with a second microorganism capable of utilizing poly-, oligo, di- and/or monosaccharides (xylanolytic and/or saccharolytic) in certain embodiments of the disclosure. In this respect, the efforts of the microorganisms are orthogonal, but complementary. Processes utilizing co-cultures, therefore, offer significant benefits over standard monoculture-based processes.

Surprisingly, the specific combination of a first microorganism belonging to the genus *Caldicellulosiruptor* and a second microorganism belonging to the genus *Thermoanaerobacter* results in higher production rates of carbon-based chemicals like ethanol and/or lactic acid than achieved by either strain alone.

By virtue of a novel integration of processing steps, commonly known as consolidated bioprocessing (CBP), aspects of the present invention provide for more efficient production of a biofuel and/or another carbon based chemical like lactic acid from cellulosic-biomass-containing raw materials like lignocellulosic biomass from plants.

The incorporation of the extremely thermophilic microorganisms in the processing of lignocellulosic biomass allows for fermentation steps to be conducted at higher temperatures, thereby improving process economics. For example, reaction kinetic is typically a function of temperature, so higher temperatures are generally associated with increases in the overall rate of production. Additionally, higher temperatures facilitate the removal of volatile products from the broth, and reduce the need for cooling of the substrate after pretreatment (a preceding step that is typically conducted at an elevated temperature). Operating CBP processes at thermophilic temperatures offers several important benefits over conventional mesophilic fermentation temperatures of 30-37° C. In particular, costs associated with having a process step dedicated to cellulase production are eliminated for CBP. Costs associated with fermenter cooling and heat-exchange before and after fermentation are also expected to be reduced for CBP. Moreover, processes featuring thermophilic biocatalysts may be less susceptible to microbial contamination as compared to processes featuring conventional mesophilic biocatalysts.

In one embodiment, the present invention provides for a method of converting hardwoods pretreated by autohydrolysis to ethanol via fermentation with a co-culture of a first anaerobic cellulolytic and of a second anaerobic saccharolytic microorganism, without the use of exogenous enzymes.

The application of the present technology has the potential to render production of carbon-based chemicals and biofuels more economically feasible and to allow a broader range of microorganisms to utilize lignocellulosic biomass. The use of cellulosic materials as sources of bioenergy is currently limited by typically requiring preprocessing of the cellulosic material. Such preprocessing methods can be expensive. Thus, methods that reduce dependence on preprocessing of cellulosic materials may have a dramatic impact on the economics of the use of recalcitrant biomass for biofuels production. One challenge in converting biomass into fermentation products is the recalcitrance and heterogeneity of the biological material.

The present inventors have found that microorganisms of the genus *Caldicellulosiruptor* in combination with microorganisms of the genus *Thermoanaerobacter* show a variety of advantageous properties for the use in the conversion of lignocellulosic biomass material to biofuel and/or carbon-based chemicals, preferably to lactic acid, in a single step process as part of a consolidated bioprocessing (CBP) system.

The specific combination of the above mentioned microorganisms in the production methods according to the present disclosure offers benefits relating to:
 a) High growing and process temperatures, resulting e.g. in a lower contamination risk in the production process and e.g. ethanol as a production product can be simultaneously distilled during the fermentation process
 b) High ethanol tolerance (tolerance of approximately 4% ethanol and more)
 c) High inhibitor tolerance
 d) Broad substrate specificity, and capable of utilizing pentoses such as xylose and arabinose and of hexoses such as glucose, mannose, fructose and galactose as well as cellulose and xylan
 e) Improved ratio of ethanol:lactate:actetate It is an advantage of the combination of the two different microorganisms that in co-culture these microorganisms are able to convert highly complex polysaccharides like cellulose and/or xylan with higher efficiency and better yields of carbon based chemicals like ethanol and/or lactic acid than either microorganism alone.

In particular, these microorganisms are extremely thermophile and show a broad substrate specificities and high natural production of ethanol and/or lactic acid. As mentioned above, carbon-based chemical fermentation at high temperatures, for example over 70° C. has many advantages over mesophilic fermentation. One advantage of thermophilic fermentation is the minimization of the problem of contamination in continuous cultures, since only a few microorganisms are able to grow at such high temperatures in un-detoxified lignocellulose biomass material.

It is also an advantage that microbial cultures comprising microorganisms of the genus *Caldicellulosiruptor* and microorganisms of the genus *Thermoanaerobacter* grow on pre-treated as well as on untreated lignocellulosic biomass material. These microbial cultures are further capable of growing and producing fermentation products on very high dry-matter concentrations of lignocellulosic biomass material.

The microbial cultures according to the present disclosure have broad substrate specificity, and are capable of utilizing pentoses such as xylose and arabinose and of hexoses such as glucose, mannose, fructose and galactose as well as utilizing cellulose and xylan. The microbial cultures further have the advantage of being extremely thermophilic and thus are capable of growing at very high temperatures resulting in high productivities and substrate conversion rates, low risk of contamination and facilitated product recovery.

Furthermore, the present inventors have found that the use of the combination of the first and the second microorganism e.g. in a microbial co-culture have a variety of advantageous properties in the conversion of polysaccharides, oligosaccharides, disaccharides and/or monosaccharides of hexoses and pentoses, in particular derived from lignocellulosic hydrolysates, to high level of ethanol and/or lactic acid while producing low level of acetic acid. In particular, these microorganisms are also extreme thermophiles and show a broad substrate specificities and high natural production of ethanol as well as lactic acid.

It is also an advantage that microbial cultures comprising extremely thermophilic microorganisms of the genus *Caldicellulosiruptor* and extremely thermophilic microorganisms of the genus *Thermoanaerobacter* grow on pre-treated as well as on untreated lignocellulosic biomass material. These microbial cultures are further capable of growing and producing fermentation products on very high dry-matter concentrations of lignocellulosic biomass material.

It was surprisingly found that microorganisms according to the present disclosure are capable of growing in a medium comprising a lignocellulosic biomass having a dry-matter content of at least 10 percent wt/wt, such as at least 15 percent wt/wt, including at least 20 percent wt/wt, and even as high as at least 25 percent wt/wt.

The microorganisms according to the present disclosure can also grow efficiently on hydrolysis products of cellulose (e.g. disaccharide cellobiose), cellulose deriven hexoses (e.g. glucose), hemicellulose deriven pentoses (e.g. xylose) and steam exploded poplar. In particular, the main products when grown on cellobiose, glucose and xylose may be ethanol and lactic acids. The main products when grown on pre-treated biomass substrates were ethanol and lactic acid, for example, when the microorganisms were grown on steam explosion treated poplar wood the ethanol yield is high. The microorganisms according to the present disclosure also grew efficiently on cellobiose.

Furthermore, the microorganisms according to the present disclosure grew efficiently on the soluble materials obtained after heat treating of lignocellulosic biomass.

Lignocellulosic biomass material and lignocellulose hydrolysates contain inhibitors such as furfural, phenols and carboxylic acids, which can potentially inhibit the fermenting organism. Therefore, it is an advantage of the microorganisms according to the present disclosure that they are tolerant to these inhibitors.

Some embodiments of the present disclosure relates to method for producing a biofuel and/or another carbon-based chemical comprising:
 a) Providing a lignocellulosic biomass
 b) Contacting the lignocellulosic biomass with a first microorganism belonging to the genus *Caldicellulosiruptor*, wherein the first microorganism converts at least a portion of the biomass into mono-, di-, and/or polysaccharides; and
 c) Contacting the lignocellulosic biomass with a second microorganism belonging to the genus *Thermoanaerobacter*, wherein the second microorganism converts at least a portion of the mono-, di-, and/or polysaccharides to a biofuel and/or another carbon-based product.

In another embodiment, a method is disclosed for simultaneous saccharification and fermentation of cellulosic material from biomass into biofuel such as ethanol or other chemicals. The method comprises treating the biomass in a closed container with a first microorganism belonging to the genus *Caldicellulosiruptor* under conditions wherein the first microorganism produces cellulolytic and/or saccharolytic enzymes sufficient to substantially convert the biomass into monosaccharides, disaccharides, oligo and/or polysaccharides and introducing a culture of a second microorganism belonging to the genus *Thermoanaerobacter*, wherein the second organism is capable of substantially converting the saccharides into biofuel and/or other carbon-based chemicals.

In particular, the first anaerobic cellulolytic microorganism has the ability to break down cellulose and hemicellulose, and to metabolize both hexose and pentose sugars resulting from the saccharification of lignocellulosic biomass. While anaerobic microorganisms can simultaneously saccharify lignocellulosic biomass and transform the full range of hexose and pentose sugars resulting from biomass into fuels and/or chemicals, the rate at which each type of hexose or pentose sugar is converted to fuels and/or chemicals will vary. Consequently, some sugars will be transformed by the anaerobic biocatalyst to fuels and/or chemicals more quickly than others. Therefore, one embodiment of the present disclosure allows for a sufficient contact time between the lignocellulosic material and the first anaerobic cellulolytic-fermenting biocatalyst to achieve substantially complete saccharification, but only partial conversion of sugars to fuels and/or products. Then the second anaerobic saccharolytic microorganism is added to the lignocellulosic biomass comprising the sugars.

In one embodiment, a first anaerobic microorganism capable of hydrolyzing cellulose, hemicellulose, or lignocellulosic material and producing mainly convertible sugars is added to a portion of a biomass and a second anaerobic microorganism capable of converting the sugars to biofuel and/or other chemical at a high rate is added simultaneously to the lignocellulosic material or with a time shift.

In another embodiment, the present disclosure relates to a method for converting lignocellulosic biomass to a biofuel or other carbon-based product, comprising the step of contacting lignocellulosic biomass with a first and a second extremely thermophilic anaerobic microorganism for a period of time at an initial temperature and an initial pH, thereby producing an amount of a biofuel and/or other carbon-based chemicals.

Furthermore, embodiments of the present disclosure pertains to microbial cultures suitable for converting lignocellulosic biomass to a biofuel and/or another carbon-based chemical comprising a first microorganism belonging to the genus *Caldicellulosiruptor* and a second microorganism belonging to the genus *Thermoanaerobacter*.

In some embodiments, the biomass material can be subjected to optional mechanical, thermochemical, and/or biochemical pretreatment prior to being used in a bioprocess for the production of fuels and other carbon-based chemicals. Mechanical processes can reduce the particle size of lignocellulosic material so that it can be more conveniently handled in the bioprocess and can increase the surface area of the feedstock to facilitate contact with chemicals/biochemicals/biocatalysts. The lignocellulosic material can also be subjected to thermal and/or chemical pretreatments to render plant polymers more accessible, but because various embodiments can incorporate multiple steps of lignocellulose treatment it may be possible to use milder and less expensive thermochemical pretreatment conditions.

Mechanical processes include, but are not limited to, washing, soaking, milling, size reduction, screening, shearing, and size classification processes. Chemical processes include, but are not limited to, bleaching, oxidation, reduction, acid treatment, base treatment, sulfite treatment, acid sulfite treatment, basic sulfite treatment, and hydrolysis. Thermal processes include, but are not limited to, sterilization, steam explosion, holding at elevated temperatures in the presence or absence of water, and freezing. Biochemical processes include, but are not limited to, treatment with enzymes and treatment with microorganisms. Various enzymes that can be utilized include cellulases, amylase, β-glucosidase, xylanase, gluconase, and other polysaccharases, lysozyme, laccase, and other lignin-modifying enzymes, lipoxygenase, peroxidase, and other oxidative enzymes, proteases, and lipases.

One or more of the mechanical, chemical, thermal and biochemical processes can be combined or used separately. Such combined processes can also include those used in the production of paper, cellulose products, microcrystalline cellulose, and cellulosics and can include pulping, kraft pulping or acidic sulfite processing. The feedstock can be a side stream or waste stream from a facility that utilizes one or more of these processes on a cellulosic, hemicellulosic or lignocellulosic material, such as a paper plant, cellulosic plant, cotton processing plant, or microcrystalline cellulose plant. The feedstock can also include cellulose-containing waste materials The pre-treatment method most often used is acid hydrolysis, where the lignocellulosic material is subjected to an acid such as sulfuric acid or sulfurous acid whereby the sugar polymers cellulose and hemicellulose are partly or completely hydrolysed to their constituent sugar monomers. Another type of lignocellulose hydrolysis is steam explosion, a process comprising heating of the lignocellulosic material by steam injection to a temperature of 175-230° C. and subsequent sudden release of pressure. A third method is wet oxidation wherein the material is treated with oxygen at 150-185° C. Yet another pretreatment can be chemical swelling of cellulose fibres in high concentrations of appropriate chemicals or solvents including but not limited to ammonia, lime, caustic soda or phosphoric acid.

The pre-treatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. The pre-treatment step may in certain embodiments be supplemented with treatment resulting in further hydrolysis of the cellulose and hemicellulose. The purpose of such an additional hydrolysis treatment is to hydrolyse oligosaccharide and possibly polysaccharide species produced during the acid hydrolysis, wet oxidation, or steam explosion of cellulose and/or hemicellulose origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid, at a temperature in the range of about 100-150° C. Enzymatic hydrolysis is typically performed by treatment with one or more appropriate carbohydrase enzymes such as cellulases, glucosidases and hemicellulases including xylanases.

In an advantageous embodiment, the isolated cells, strains, microorganisms, compositions and microbial cultures convert lignocellulosic biomass material which has been only mechanically treated to biofuel and/or carbon-based chemicals, preferably to ethanol and/or lactic acid, preferably in a single step process as part of a consolidated bioprocessing (CBP) system.

In other advantageous embodiments, the lignocellulosic biomass is pretreated with mechanical comminution and a subsequent treatment with sulfurous acid or its anhydride under heat and pressure with a sudden release of pressure. In advantageous embodiments, the lignocellulosic biomass is milled before converted in biofuels and/or carbon-based chemicals like lactic acid. In one embodiment, the lignocellulosic biomass is pretreated biomass from *Populus* spp, preferably pretreated with steam explosion. In another embodiment, the lignocellulosic biomass is pretreated biomass from *Miscanthus* spp, preferably pretreated with steam explosion.

In some embodiments, the anaerobic microorganism according to the present disclosure can ferment biomass directly without the need of a pretreatment.

In some embodiments, the lignocellulosic biomass may be pretreated, such as by thermal, mechanical, and/or chemical means. Such pretreatment may at least partially hydrolyze carbohydrates or proteins present, disrupt cellular structure, increase the surface area, or render carbohydrates more accessible to microorganisms or enzymes.

In some embodiments, process steps include—1) contacting a pre-treated biomass material under anaerobic conditions with a first anaerobic microorganism belonging to the genus of *Caldicellulosiruptor*, where the bacterium is capable of converting at least a portion of the biomass into carbohydrates like monosaccharides, disaccharides, oligosaccharides, polysaccharides, alcohols and/or lactic acid, 2) contacting the resulting treated feedstock with an anaerobic saccharolytic microorganism belonging to the genus *Thermoanaerobacter* that is capable of fermenting at least a portion of the carbohydrates to fuels and/or other chemicals, 3) separating the fermentation product(s), e.g. by distillation.

With the methods, the microorganisms and/or the microbial cultures according to the present disclosure a number of different fermentation products are generated, including acids, alcohols, ketones and hydrogen. In one embodiment, the alcohol is selected from the group consisting of ethanol, butanol, propanol, methanol, propanediol and butanediol. In a further embodiment the acid is an organic acid like lactic acid, propionic acid, acetic acid, succinic acid, butyric acid or formic acid and the ketone is acetone. In advantageous embodiments a biofuel, in particular ethanol and/or lactic acid is produced.

To produce a fermentation product, the lignocellulosic biomass is contacted with a first microorganism belonging to the genus *Caldicellulosiruptor*, in particular with a novel species of the genus *Caldicellulosiruptor* or novel subspecies of *Caldicellulosiruptor saccharolyticus*. In one embodiment, the *Caldicellulosiruptor* microorganisms are cellulolytic and xylanolytic.

For example, the genus *Caldicellulosiruptor* includes different species of extremely thermophilic (temperature optima for growth higher than 70° C.) cellulolytic and hemicellulolytic strictly anaerobic non-sporeforming bacteria. The first bacterium of this genus, *Caldicellulosiruptor saccharolyticum* strain Tp8T (DSM 8903) has a temperature optimum of 70° C. and was isolated from a thermal spring in New Zealand (Rainey et al. 1994; Sissons et al. 1987). It hydrolyses a variety of polymeric carbohydrates with the production of acetate, lactate and trace amounts of ethanol (Donnison et al. 1988). Phylogenetic analysis showed that it constitutes a novel lineage within the *Bacillus/Clostridium* subphylum of the Gram-positive bacteria (Rainey et al. 1994).

In advantageous embodiments, the microorganism belonging to the genus *Caldicellulosiruptor* is selected from the group consisting of the microorganisms listed in table 1.

TABLE 1

| Genus | Species | Name | DSMZ accession number | Deposition date | 16SrDNA SEQ ID NO. |
|---|---|---|---|---|---|
| *Caldicellulo-siruptor* | sp. | DIB004C | DSM 25177 | 15 Sep. 2011 | 1 |
| *Caldicellulo-siruptor* | sp. | DIB041C | DSM 25771 | 15 Mar. 2012 | 2 |
| *Caldicellulo-siruptor* | sp. | DIB087C | DSM25772 | 15 Mar. 2012 | 3 |
| *Caldicellulo-siruptor* | sp. | DIB101C | DSM 25178 | 15 Sep. 2011 | 4 |
| *Caldicellulo-siruptor* | sp. | DIB103C | DSM 25773 | 15 Mar. 2012 | 5 |
| *Caldicellulo-siruptor* | sp. | DIB104C | DSM 25774 | 15 Mar. 2012 | 6 |
| *Caldicellulo-siruptor* | sp. | DIB107C | DSM 25775 | 15 Mar. 2012 | 7 |

The strains listed in table 1 have been deposited in accordance with the terms of the Budapest Treaty on the notified deposition dates with DSMZ—Deutsche Sammlung von Mikroorganismen and Zellkulturen GmbH, Inhoffenstr. 7B, 38124 Braunschweig, Germany, under the above notified DSMZ accession numbers by DIREVO Industrial Biotechnology GmbH, Nattermannallee 1, 50829 Cologne (DE).

In an advantageous embodiment, the first microorganism belonging to the genus *Caldicellulosiruptor* comprises a 16S rDNA sequence selected from the group consisting of: SEQ ID NO 1, SEQ ID NO 2, SEQ ID NO 3, SEQ ID NO 4, SEQ ID NO 5, SEQ ID NO 6 and SEQ ID NO 7 and any combinations thereof.

In one embodiment, the first microorganism belonging to the genus *Caldicellulosiruptor* comprises a 16S rDNA sequence at least 99, at least 99.3, at least 99.5, at least, 99.7, at least 99.9, at least 99.99 percent identical to SEQ ID NO 1. In further embodiments, the first microorganism belonging to the genus *Caldicellulosiruptor* comprises a 16S rDNA sequence at least 99, at least 99.3, at least 99.5, at least, 99.7, at least 99.9, at least 99.99 percent identical to a sequence selected from SEQ ID NO 2, SEQ ID NO 3, SEQ ID NO 4, SEQ ID NO 5, SEQ ID NO 6 or SEQ ID NO 7 and any combination thereof.

In another embodiment, *Caldicellulosiruptor* sp. DIB004C (DSMZ Accession number 25177) and/or a *Caldicellulosiruptor* sp. strain listed in table 1, cells derived there from, mutants there from, progenies or homologs are used as the first microorganism in the production methods according to the present disclosure.

In an advantageous embodiment, the first microorganism used in the methods according to the present disclosure refers to a microorganism which preferably has one or more of the following characteristics:

a) it is a microorganism of the genus *Caldicellulosiruptor*;

b) in a DNA-DNA hybridization assay, it shows a DNA-DNA relatedness of at least 70%, preferably at least 90%, at least 95%, more preferred at least 98%, most preferred at least 99% with one *Caldicellulosiruptor* sp. strain listed in table 1, respectively; and/or c) it displays a level of 16S rDNA gene sequence similarity of at least 98%, preferably at least 99% or at least 99.5%, more preferably 100% with one *Caldicellulosiruptor* sp. strain listed in table 1, respectively; and/or d) it is capable of growing in high temperature conditions above 70° C., and or e) it is a Gram-positive bacterium.

Preferably, at least two or at least three, and more preferred all of the above defined criteria a) to e) are fulfilled.

The used *Caldicellulosiruptor* microorganisms according to the present disclosure have several highly advantageous characteristics needed for the conversion of lignocellulosic biomass material. Thus, these base strains possess all the genetic machinery for the hydrolysis of cellulose and hemicelluloses and for the conversion of both pentose and hexose sugars to various fermentation products such as lactic acid and ethanol. As will be apparent from the below examples, the examination of the complete 16S rDNA sequence showed that the seven strains of *Caldicellulosiruptor* sp. listed in table 1 may all be related to *Caldicellulosiruptor saccharolyticus* although the 16S rDNA sequences clearly place them in a separate subspecies or even a different species In a preferred embodiment, the first microorganism used in the methods according to the present disclosure is:

a) *Caldicellulosiruptor* sp. DIB004C, deposited on Sep. 15, 2011 under the accession number DSM 25177 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from *Caldicellulosiruptor* sp. DIB004C or c) a *Caldicellulosiruptor* sp. DIB004C homolog.

In another preferred embodiment, the first microorganism used in the methods according to the present disclosure is:

a) Any *Caldicellulosiruptor* sp. strain listed in table 1 except *Caldicellulosiruptor* DIB004C, deposited under the respective accession number indicated in table 1 according to the requirements of the Budapest Treaty at the Deutsche Sammlung von Mikroorganismen und Zellkulturen (DSMZ), Inhoffenstraβe 7B, 38124 Braunschweig (DE) by DIREVO Industrial Biotechnology GmbH, Nattermannallee 1, 50829 Cologne (DE), b) a microorganism derived from such *Caldicellulosiruptor* sp. strain or c) a homolog of such *Caldicellulosiruptor* sp. strain All strains listed in table 1 belong to the genus *Caldicellulosiruptor* and are strictly anaerobic, non-sporeforming, non-motile, gram-positive bacteria. Cells are straight rods 0.4-0.5 μm by 2.0-4.0 μm, occurring both singly and in pairs. After 7 days incubation at 72° C. on solid medium with agar and cellulose as substrate all seven strains form circular milky colonies of 0.5-1 mm in diameter. Clearing zones around the colonies are produced indicating cellulose degradation.

In advantageous embodiments, the second microorganism is a novel species of the genus *Thermoanaerobacter*. The *Thermoanaerobacter* sp. strains according to the present disclosure as listed in table 2 are saccharolytic (ferment hexoses and pentoses to ethanol, lactate and traces of acetate). Five strains listed in table 2 are related to *Thermoanaerobacter mathranii* and three strains are related to *Thermoanaerobacter thermohydrosulfuricus*.

For example, the genus *Thermoanaerobacter* includes different species of extremely thermophilic (temperature optima for growth higher than 70° C.) and thermophilic hemicellulolytic and saccharolytic strictly anaerobic bacteria (Lee et al. 1993). *Thermoanaerobacter mathranii* DSM 11426 is an extremely thermophilic bacterium. It has a temperature optimum between 70 and 75° C. and was isolated from a hot spring in Iceland (Larsen et al. 1997). It uses a number of sugars as carbon sources, but did not utilize microcrystalline cellulose. Fermentation end products on xylose were ethanol, acetate, low amounts of lactate, $CO_2$, and $H_2$ (Larsen et al. 1997). *Thermoanaerobacter brockii* subsp. *finnii* is a thermophilic saccharolytic bacterium. It has a temperature optimum between 55 and 60° C. and was isolated from an oil field at a depth of 2,100 m (Cayol et al. 1995). It uses a number of sugars as carbon sources, but cannot utilize xylan or cellulose. Fermentation end products on glucose were lactate, acetate, ethanol, $H_2$, and $CO_2$ (Coyol et al. 1995).

In advantageous embodiments, the microorganism belonging to the genus *Thermoanaerobacter* is selected from the group consisting of the microorganisms listed in table 2.

TABLE 2

| Genus | Species | Name | DSMZ accession number | Deposition date | 16SrDNA SEQ ID NO. |
|---|---|---|---|---|---|
| Thermoanaerobacter | sp. | DIB004G | DSM 25179 | 15 Sep. 2011 | 8 |
| Thermoanaerobacter | sp. | DIB087G | DSM 25777 | 15 Mar. 2012 | 9 |
| Thermoanaerobacter | sp. | DIB097X | DSM 25308 | 27 Feb. 2011 | 10 |
| Thermoanaerobacter | sp. | DIB101G | DSM 25180 | 15 Sep. 2011 | 11 |
| Thermoanaerobacter | sp. | DIB101X | DSM 25181 | 15 Sep. 2011 | 12 |
| Thermoanaerobacter | sp. | DIB103X | DSM 25776 | 15 Mar. 2012 | 13 |
| Thermoanaerobacter | sp. | DIB104X | DSM 25778 | 15 Mar. 2012 | 14 |
| Thermoanaerobacter | sp. | DIB107X | DSM 25779 | 15 Mar. 2012 | 15 |

The strains listed in table 2 have been deposited in accordance with the terms of the Budapest Treaty on the notified deposition dates with DSMZ—Deutsche Sammlung von Mikroorganismen and Zellkulturen GmbH, Inhoffenstr. 7B, 38124 Braunschweig, Germany, under the above notified DSMZ accession numbers by DIREVO Industrial Biotechnology GmbH, Nattermannallee 1, 50829 Cologne (DE).

In one embodiment, the second microorganism belonging to the genus *Thermoanaerobacter* comprises a 16S rDNA sequence at least 99, at least 99.3, at least 99.5, at least, 99.7, at least 99.9, at least 99.99 percent identical to SEQ ID NO 8. In further embodiments, the first microorganism belonging to the genus *Thermoanaerobacter* comprises a 16S rDNA sequence at least 99, at least 99.3, at least 99.5, at least, 99.7, at least 99.9, at least 99.99 percent identical to a sequence selected from SEQ ID NO 9, SEQ ID NO 10, SEQ ID NO 11, SEQ ID NO 12, SEQ ID NO 13, SEQ ID NO 14 or SEQ ID NO 15, and any combination thereof.

In other embodiments, the *Thermoanaerobacter* sp. strains listed in table 2, cells derived there from, mutants there from, progenies or homologs are used as the second microorganism in the production methods according to the present disclosure.

In an advantageous embodiment, *Thermoanaerobacter* sp. DIB004G (DSMZ Accession number 25179) and/or *Thermoanaerobacter* sp. DIB101G (DSMZ Accession number 25180), cells derived there from, mutants there from, progenies or homologs are used as the second microorganism in the production methods according to the present disclosure.

The second microorganism can be *Thermoanaerobacter* sp. DIB004G and/or any *Thermoanaerobacter* strain listed in table 2 that contains 16S rDNA sequences 100 percent and/or 99.99 percent identical to any of the sequences SEQ ID 8-SEQ ID 15, respectively.

In further embodiments, the lignocellulosic biomass is contacted and/or treated with a second microorganism having one or more of the following characteristics:
a) it is a microorganism of the genus *Thermoanaerobacter*; and/or
b) in a DNA-DNA hybridization assay, it shows a DNA-DNA relatedness of at least 70%, preferably at least 90%, at least 95%, more preferred at least 98%, most preferred at least 99% with any of the *Thermoanaerobacter* sp. strains listed in table 2 with the respectively indicated accession numbers and deposition dates; and/or
c) it displays a level of 16S rDNA gene sequence similarity of at least 98%, preferably at least 99% or at least 99.5%, more preferably 100% with any of the *Thermoanaerobacter* sp. strains listed in table 2 with the respectively indicated accession numbers and deposition dates, respectively; and/or
d) it is capable of growing in high temperature conditions above 70° C., and/or
e) it is a Gram-positive bacterium.

Preferably, at least two or at least three, and more preferred all of the above defined criteria a) to e) are fulfilled.

In another advantageous embodiment, the second microorganism used in the methods according to the present disclosure is:
a) *Thermoanaerobacter* sp. DIB004G, deposited on Sep. 15, 2011 under the accession number DSM 25179 according to the requirements of the Budapest Treaty at the Deutsche Sammlung von Mikroorganismen and Zellkulturen (DSMZ), Inhoffenstraße 7B, 38124 Braunschweig (DE) by DIREVO Industrial Biotechnology GmbH, Nattermannallee 1, 50829 Cologne, Germany (DE), or
b) a microorganism derived from *Thermoanaerobacter* sp. DIB004G, or
c) a *Thermoanaerobacter* sp. DIB004G homolog.

In another advantageous embodiment, the second microorganism used in the methods according to the present disclosure is:
a) any *Thermoanaerobacter* sp. strain except *Thermoanaerobacter* sp. DIB004G listed in table 2 with their respectively indicated deposition dates and accession numbers deposited according to the requirements of the Budapest Treaty at the Deutsche Sammlung von Mikroorganismen und Zellkulturen (DSMZ), Inhoffenstraße 7B, 38124 Braunschweig (DE) by DIREVO Industrial Biotechnology GmbH, Nattermannallee 1, 50829 Cologne, Germany (DE), or
b) a microorganism derived from either of these *Thermoanaerobacter* sp. strains or
c) a homolog of either of these strains All *Thermoanaerobacter* sp. strains listed in table 2 belong to the genus *Thermoanaerobacter* and are extremely thermophilic (growth at temperatures higher than 70° C.), saccharolytic, strictly anaerobic and Gram-positive bacteria. Cells are straight rods 0.3-0.4 µm by 2.0-6.0 µm, occurring both singly and in pairs. DIB004G and DIB101G grow on various sugars as substrate, including cellobiose, glucose, and xylose. The main fermentation products on these sugars are ethanol and lactate. Trace amounts of acetate are also formed.

In a further embodiment, *Thermoanaerobacter* sp. DIB101X deposited as DSM 25181 and/or *Thermoanaerobacter* sp. DIB97X deposited as DSM 25308, cells derived there from, mutants there from, progenies or homologs are used as the second microorganism in the production methods according to the present disclosure.

It is a great advantage that *Thermoanaerobacter* sp. DIB101X deposited as DSM 25181 and *Thermoanaerobacter* sp. DIB97X deposited as DSM 25308 are xylanolytic and saccharolytic (ferment hemicelluloses, e.g. xylan, hexoses and pentoses to ethanol, lactate and small amounts of acetate).

The strain DIB101X has been deposited in accordance with the terms of the Budapest Treaty on Sep. 15, 2011 with DSMZ—Deutsche Sammlung von Mikroorganismen und Zellkulturen GmbH, Inhoffenstr. 7B, 38124 Braunschweig, Germany under DSMZ accession number DSM 25181 by DIREVO Industrial Biotechnology GmbH, Nattermannallee 1, 50829 Cologne, Germany (DE).

The strain DIB97X has been deposited in accordance with the terms of the Budapest Treaty on Oct. 27, 2011 with DSMZ—Deutsche Sammlung von Mikroorganismen und Zellkulturen GmbH, Inhoffenstr. 7B, 38124 Braunschweig, Germany under DSMZ accession number DSM 25308 by DIREVO Industrial Biotechnology GmbH, Nattermannallee 1, 50829 Cologne, Germany (DE).

In further embodiments, the lignocellulosic biomass is contacted and/or treated with a second microorganism having one or more of the following characteristics:
a) it is a microorganism of the genus *Thermoanaerobacter*; and/or
b) in a DNA-DNA hybridization assay, it shows a DNA-DNA relatedness of at least 70%, preferably at least 90%, at least 95%, more preferred at least 98%, most preferred at least 99% with *Thermoanaerobacter* sp. DIB101X or *Thermoanaerobacter* sp. DIB97X deposited as DSM 25181 or DSM 25308, respectively; and/or
c) it displays a level of 16S rDNA gene sequence similarity of at least 98%, preferably at least 99% or at least 99.5%, more preferably 100% with *Thermoanaerobacter* sp. DIB101X or *Thermoanaerobacter* sp. DIB97X deposited as DSM 25181 or DSM 25308, respectively; and/or
d) it is capable of growing in high temperature conditions above 70° C., and/or
e) it is a Gram-positive bacterium.

Preferably, at least two or at least three, and more preferred all of the above defined criteria a) to e) are fulfilled.

In another advantageous embodiment, the second microorganism used in the methods according to the present disclosure is:
d) *Thermoanaerobacter* sp. DIB101X, deposited on Sep. 15, 2011 under the accession number DSM 25181 according to the requirements of the Budapest Treaty at the Deutsche Sammlung von Mikroorganismen und Zellkulturen (DSMZ), Inhoffenstraße 7B, 38124 Braunschweig (DE) by DIREVO Industrial Biotechnology GmbH, Nattermannallee 1, 50829 Cologne, Germany (DE), or e) a microorganism derived from *Thermoanaerobacter* sp. DIB101X, or f) a *Thermoanaerobacter* sp. DIB101X homolog.

In another advantageous embodiment, the second microorganism used in the methods according to the present disclosure is:

d) *Thermoanaerobacter* sp. DIB97X, deposited on Oct. 27, 2011 under the accession number DSM 25308 according to the requirements of the Budapest Treaty at the Deutsche Sammlung von Mikroorganismen und Zellkulturen (DSMZ), Inhoffenstraße 7B, 38124 Braunschweig (DE) by DIREVO Industrial Biotechnology GmbH, Nattermannallee 1, 50829 Cologne, Germany (DE), or e) a microorganism derived from *Thermoanaerobacter* sp. DIB97X or f) a *Thermoanaerobacter* sp. DIB97X homolog.

*Thermoanaerobacter* sp. DIB101X (DSM 25181) and DIB97X (DSM 25308) belong to the genus *Thermoanaerobacter* and are extremely thermophilic (growth at temperatures higher than 70° C.), xylanolytic and saccharolytic, strictly anaerobic, Gram-positive bacteria. Cells are straight rods 0.3-0.4 µm by 2.0-6.0 µm, occurring both singly and in pairs. DIB101X and DIB97X grow on various sugars as substrate, including xylan, xylose, cellobiose, and glucose. The main fermentation products on these substrates are ethanol and lactate. Low amounts of acetate are also formed.

As is apparent from the following, the preferred strains of the present disclosure have been deposited. Other cells, strains, bacteria, microorganisms and/or microbial cultures of the present disclosure can therefore be obtained by mutating the deposited strains and selecting derived mutants having enhanced characteristics. Desirable characteristics include an increased range of sugars that can be utilized, increased growth rate, ability to produce higher amounts of fermentation products such as ethanol and/or lactic acid, etc. Suitable methods for mutating bacteria strains and selecting desired mutants are described in Functional analysis of Bacterial genes: A practical Manual, edited by W. Schumann, S. D. Ehrlich & N. Ogasawara, 2001.

In advantageous embodiments the microorganisms may be modified in order to obtain mutants or derivatives with improved characteristics. Thus, in one embodiment there is provided a bacterial strain according to the disclosure, wherein one or more genes have been inserted, deleted or substantially inactivated. The variant or mutant is typically capable of growing in a medium comprising a lignocellulosic biomass material.

In another embodiment, there is provided a process for preparing variants or mutants of the microorganisms according to the present disclosure, wherein one or more genes are inserted, deleted or substantially inactivated as described herein.

In some embodiments one or more additional genes are inserting into a microorganism according to the present disclosure, in particular in the first microorganism belonging to the genus *Caldicellulosiruptor*, in particular in *Caldicellulosiruptor* sp. DIB004C (DSM 25177) and/or another *Caldicellulosiruptor* sp. strain listed in table 1. Thus, in order to improve the yield of the specific fermentation product, it may be beneficial to insert one or more genes encoding a polysaccharase into the strain according to the invention. Hence, in specific embodiments there is provided a strain and a process according to the invention wherein one or more genes encoding a polysaccharase which is selected from cellulases (such as EC 3.2.1.4); beta-glucanases, including glucan-1,3 beta-glucosidases (exo-1,3 beta-glucanases, such as EC 3.2.1.58), 1,4-beta-cellobiohydrolases (such as EC 3.2.1.91) and endo-1,3(4)-beta-glucanases (such as EC 3.2.1.6); xylanases, including endo-1,4-beta-xylanases (such as EC 3.2.1.8) and xylan 1,4-beta-xylosidases (such as EC 3.2.1.37); pectinases (such as EC 3.2.1.15); alpha-glucuronidases, alpha-L-arabinofuranosidases (such as EC 3.2.1.55), acetylesterases (such as EC 3.1.1.-), acetylxylanesterases (such as EC 3.1.1.72), alpha-amylases (such as EC 3.2.1.1), beta-amylases (such as EC 3.2.1.2), glucoamylases (such as EC 3.2.1.3), pullulanases (such as EC 3.2.1.41), beta-glucanases (such as EC 3.2.1.73), hemicellulases, arabinosidases, mannanases including mannan endo-1,4-beta-mannosidases (such as EC 3.2.1.78) and mannan endo-1,6-alpha-mannosidases (such as EC 3.2.1.101), pectin hydrolases, polygalacturonases (such as EC 3.2.1.15), exopolygalacturonases (such as EC 3.2.1.67) and pectate lyases (such as EC 4.2.2.10), are inserted.

In accordance with the present disclosure, a method of producing a fermentation product comprising culturing a strain according to the invention under suitable conditions is also provided.

The strains according to the disclosure are strictly anaerobic microorganisms, and hence it is preferred that the fermentation product is produced by a fermentation process performed under strictly anaerobic conditions. Additionally, the microorganisms according to the disclosure are extremely thermophillic microorganisms, and therefore the process may perform optimally, when it is operated at temperature in the range of about 45-95 degrees centigrade, such as the range of about 50-90 degrees centigrade, including the range of about 60-85 degrees centigrade, such as the range of about 65-75 degrees centigrade. In an advantageous embodiment the temperature is 70° C. and higher.

For the production of certain fermentation products, it may be useful to select a specific fermentation process, such as batch fermentation process, including a fed-batch process or a continuous fermentation process. Also, it may be useful to select a fermentation reactor such as an immobilized cell reactor, a fluidized bed reactor or a membrane bioreactor.

In an advantageous embodiment, the microbial culture comprises *Caldicellulosiruptor* sp. DIB004C (DSMZ Accession number 25177) as the first microorganism and *Thermoanaerobacter* sp. DIB004G (DSM 25179) as the second microorganism.

In another advantageous embodiment, the microbial culture comprises *Caldicellulosiruptor* sp. DIB004C (DSMZ Accession number 25177) as the first microorganism and *Thermoanaerobacter* sp. DIB097X (DSM 25308) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB004G (DSM 25179) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB004G (DSM 25179) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB004G (DSM 25179) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB004G (DSM 25179) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB004G (DSM 25179) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB087G (DSM 25777) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB087G (DSM 25777) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB087G (DSM 25777) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB087G (DSM 25777) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB004G (DSM 25179) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB087G (DSM 25777) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB087G (DSM 25777) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB097X (DSM 25308) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB097X (DSM 25308) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB097X (DSM 25308) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB097X (DSM 25308) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB097X (DSM 25308) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB097X (DSM 25308) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB097X (DSM 25308) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB101G (DSM 25180) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB101G (DSM 25180) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB101G (DSM 25180) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB101G (DSM 25180) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB101G (DSM 25180) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB101G (DSM 25180) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB101G (DSM 25180) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB101X (DSM 25181) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB101X (DSM 25181) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB101X (DSM 25181) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB101X (DSM 25181) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB101X (DSM 25181) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB101X (DSM 25181) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB101X (DSM 25181) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB103X (DSM 25776) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB103X (DSM 25776) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB103X (DSM 25776) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB103X (DSM 25776) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB103X (DSM 25776) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB103X (DSM 25776) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB103X (DSM 25776) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB104X (DSM 25778) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB104X (DSM 25778) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB104X (DSM 25778) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB104X (DSM 25778) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB104X (DSM 25778) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB104X (DSM 25778) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB104X (DSM 25778) as the second microorganism.

In an advantageous embodiment, the microbial culture comprises *Caldicellulosiruptor* sp. DIB004C (DSMZ Accession number 25177) as the first microorganism and *Thermoanaerobacter* sp. DIB107X (DSM 25779) as the second microorganism.

In another advantageous embodiment, the microbial culture comprises *Caldicellulosiruptor* sp. DIB041C (DSMZ Accession number 25771) as the first microorganism and *Thermoanaerobacter* sp. DIB107X (DSM 25779) as the second microorganism.

In another advantageous embodiment, the microbial culture comprises *Caldicellulosiruptor* sp. DIB087C (DSMZ Accession number 25772) as the first microorganism and *Thermoanaerobacter* sp. DIB107X (DSM 25779) as the second microorganism.

In another advantageous embodiment, the microbial culture comprises *Caldicellulosiruptor* sp. DIB101C (DSMZ Accession number 25178) as the first microorganism and *Thermoanaerobacter* sp. DIB107X (DSM 25779) as the second microorganism.

In another advantageous embodiment, the microbial culture comprises *Caldicellulosiruptor* sp. DIB103C (DSMZ Accession number 25773) as the first microorganism and *Thermoanaerobacter* sp. DIB107X (DSM 25779) as the second microorganism.

In another advantageous embodiment, the microbial culture comprises *Caldicellulosiruptor* sp. DIB104C (DSMZ Accession number 25774) as the first microorganism and *Thermoanaerobacter* sp. DIB107X (DSM 25779) as the second microorganism.

In another advantageous embodiment, the microbial culture comprises *Caldicellulosiruptor* sp. DIB107C (DSMZ Accession number 25775) as the first microorganism and *Thermoanaerobacter* sp. DIB107X (DSM 25779) as the second microorganism.

In certain embodiments, the microorganisms used in the methods of the present disclosure grow and produce ethanol most efficiently at a certain initial temperature. As mentioned above, it is an advantage of the methods of the present disclosure that the temperature can be high, preferably higher than 65° C., more preferably 70° C. and higher until a maximum temperature of at 90° C., preferably 80° C., more preferably 75° C. since the used microorganisms are extremely thermophilic. This results in lower contamination risk and faster reaction times.

In certain embodiments, the disclosure relates to any one of the above-mentioned methods, wherein the period of time is about 10 hours to about 300 hours. In certain embodiments, the disclosure relates to any one of the above-mentioned methods, wherein the period of time is about 50 hours to about 200 hours. In certain embodiments, the disclosure relates to any one of the above-mentioned methods, wherein the period of time is about 80 hours to about 160 hours. In certain embodiments, the disclosure relates to any one of the above-mentioned methods, wherein the period of time is about 80 hours (h), about 85 h, about 90 h, about 95 h, about 100 h, about 105 h, about 110 h, about 115 h, about 120 h, about 125 h, about 130 h, about 135 h, about 140 h, about 145 h, about 150 h, about 155 h, or about 160 h.

In certain embodiments, the disclosure relates to any one of the above-mentioned methods, wherein the period of time is about 120 hours. In certain embodiments, the disclosure relates to any one of the above-mentioned methods, wherein the initial temperature is about 45° C. to about 80° C. In certain embodiments, the invention relates to any one of the above-mentioned methods, wherein the initial temperature is about 65° C. to about 80° C. In certain embodiments, the disclosure relates to any one of the above-mentioned methods, wherein the initial temperature is about 70° C. to about 75° C. In certain embodiments, the disclosure relates to any one of the above-mentioned methods, wherein the initial temperature is about 72° C.

In certain embodiments, the disclosure relates to any one of the above-mentioned methods, wherein the initial pH is between about 5 and about 9. In certain embodiments, the disclosure relates to any one of the above-mentioned methods, wherein the initial pH is between about 6 and about 8. In certain embodiments, the disclosure relates to any one of the above-mentioned methods, wherein the initial pH is about 5, about 5.5, about 6, about 6.5, about 7, about 7.5, about 8, about 8.5, or about 9. In certain embodiments, the disclosure relates to any one of the above-mentioned methods, wherein the initial pH is about 6, about 6.5, about 7, about 7.5, or about 8.

As mentioned above, the used microbial co-culture for producing the fermentation product from biomass shows several features that distinguishes them from currently used microorganisms: (i) high yield and low product inhibition, (ii) simultaneous utilization of lignocellolytic biomass material and/or sugars, and (iii) growth at elevated temperatures. The microorganisms in the microbial co-culture are robust thermophilic organisms with a decreased risk of contamination. They efficiently convert an extraordinarily wide range of biomass components to carbon-based chemicals like lactic acid or ethanol.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The following methods and examples are offered for illustrative purposes only, and are not intended to limit the scope of the present disclosure in any way.

METHODS AND EXAMPLES

In the following examples, materials and methods of the present disclosure are provided including the determination of properties of the strains according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1: Isolation and Cultivation

All procedures for enrichment and isolation of strains employed anaerobic technique for strictly anaerobic bacteria (Hungate 1969). The strains were enriched from environmental samples at temperatures higher than 70° C. with crystalline cellulose and beech wood as substrate. Isolation was performed by picking colonies grown on solid agar medium at 72° C. in Hungate roll tubes (Hungate 1969).

The cells are cultured under strictly anaerobic conditions applying the following medium:

| Basic medium | | |
|---|---|---|
| NH4Cl | 1.0 | g |
| NaCl | 0.5 | g |
| MgSO4 x 7H2O | 0.3 | g |
| CaCl2 x 2H2O | 0.05 | g |
| NaHCO3 | 0.5 | g |
| K2HPO4 | 1.5 | g |
| KH2PO4 | 3.0 | g |
| Yeast extract (bacto, BD) | 0.5 | g |
| Cellobiose | 5.0 | g |
| Vitamins (see below) | 1.0 | ml |
| Trace elements (see below) | 0.5 | ml |
| Resazurin | 1.0 | mg |
| Na2S x 9H2O | 0.75 | g |
| Deionized water | 1000.0 | ml |
| Trace elements stock solution | | |
| $NiCl_2$ x $6H_2O$ | 2 | g |
| $FeSO_4$ x $7H_2O$ | 1 | g |
| NH4Fe(III) citrate, brown, 21.5% Fe | 10 | g |
| $MnSO_4$ x $H_2O$ | 5 | g |
| $CoCl_2$ x $6H_2O$ | 1 | g |
| $ZnSO_4$ x $7H_2O$ | 1 | g |
| $CuSO_4$ x $5H_2O$ | 0.1 | g |
| $H_3BO_3$ | 0.1 | g |
| $Na_2MoO_4$ x $2H_2O$ | 0.1 | g |
| $Na_2SeO_3$ x $5H_2O$ | 0.2 | g |
| $Na_2WoO_4$ x $2H_2O$ | 0.1 | g |
| Distilled water | 1000.0 | ml |
| Add 0.5 ml of the trace elements stock solution to 1 liter of the medium | | |
| Vitamin stock solution | | |
| nicotinic acid | 200 | mg |
| cyanocobalamin | 25 | mg |
| p-aminobenzoic acid (4-aminobenzoic acid) | 25 | mg |
| calcium D-pantothenate | 25 | mg |
| thiamine-HCl | 25 | mg |
| riboflavin | 25 | mg |
| lipoic acid | 25 | mg |
| folic acid | 10 | mg |

| | | |
|---|---|---|
| biotin | 10 | mg |
| pyridoxin-HCl | 10 | mg |
| Distilled water | 200.0 | ml |
| Add 1 ml of the vitamine stock solution to 1 liter of the medium | | |

All ingredients except sulfide are dissolved in deionized water and the medium is flushed with nitrogen gas (purity 99.999%) for 20 min at room temperature. After addition of sulfide, the pH-value is adjusted to 7.0 at room temperature with 1 M HCl. The medium is then dispensed into 100 ml serum flasks under nitrogen atmosphere and the vessels are tightly sealed. After autoclaving at 121° C. for 20 min pH-value should be in between 6.8 and 7.0.

Glucose, xylan, steam explosion treated substrates and microcrystalline cellulose Avicel are added to serum flasks to a concentration of 10 g/l (dry weight) prior autoclaving. Subsequent to autoclaving, cultures are inoculated by injection of a seed culture through the seal septum and incubated in an incubator at 72° C. and 100 rpm for the time indicated. Seed cultures were grown for 48 h on microcrystalline cellulose (cellulolytic strains, e.g. DIB004C, DIB101C), glucose (saccharolytic strains, e.g. DIB004G, DIB101G) or xylan (saccharolytic/xylanolytic strains, e.g. DIB97X, DIB101X).

Example 2: HPLC

Sugars and fermentation products were quantified by HPLC-RI using a Via Hitachi LaChrom Elite (Hitachi corp.) fitted with a Rezex ROA Organic Acid H+ (Phenomenex). The analytes were separated isocratically with 2.5 mM $H_2SO_4$ and at 65° C.

Example 3: Phylogenetic Analysis of 16S rDNA Genes

Genomic DNA was isolated from cultures grown as described above and 16SrDNA amplified by PCR using 27F (AGAGTTTGATCMTGGCTCAG) as forward and 1492R (GGTTACCTTGTTACGACTT) as reverse primer. The resulting products were sequenced and the sequences analyzed using the Sequencher 4.10.1 software (Gene Codes Corporation). The NCBI database was used for BLAST procedures. Phylogenetic 16S rRNA gene analyses were performed by the neighbor-joining method (Saitou and Nei 1987) using the program Mega 4 (Tamura et al. 2007)

Example 4: Production of Ethanol and Lactate on Different Substrates

Experiments on growth and fermentation of steam explosion treated substrates DDGS-STEX, BP-STEX, SCB-STEX, CORNST-STEX, CORNPL-STEX, MISC-STEX, SORG-STEX, SPR-STEX as well as microcrystalline cellulose Avicel were performed by cultivation in sealed 100 ml flasks with 30 ml medium described in Example 1. Strains DIB004C and DIB101C grew well on all these substrates including microcrystalline cellulose. Strains DIB004G, DIB101G, DIB97X and DIB101X grew well on all steam explosion treated substrates, but could not grow on microcrystalline cellulose.

All strains grew well on media containing 20 g/l (dry weight) $SO_2$ steam explosion treated poplar wood (2% PO-STEX) when cultivated in 100 ml sealed flasks with 30 ml medium described in Example 1. FIG. 1 shows the results of the product formation of the strains *Caldicellulosiruptor* sp. DIB004C (A), *Thermoanaerobacter* sp. DIB004G (B) alone and in co-culture of both strains (C) for various steam explosion treated technical substrates. For each substrate, 10 g/l dry weight concentrations were applied. Abbreviations for the individual substrates are DDGS-STEX: Dried distillers grains and solubles, pretreated by steam explosion; BP-STEX: beet pulp, pretreated by steam explosion; SCB-STEX: sugar cane bagasse, pretreated by steam explosion; CORNST-STEX: corn stalks, pretreated by steam explosion; CORNPL-STEX: whole corn plants incl. stalk, cob and kernel, pretreated by steam explosion; MISC-STEX: *Miscanthus* plants, pretreated by steam explosion; SORG-STEX: sweet sorghum whole plant. pretreated by steam explosion; SPR-STEX: spruce wood, pretreated by steam explosion The main fermentation products were ethanol, acetate and lactate. As clearly indicated in FIG. 1 showing product concentrations after 7 days of cultivation for (A) DIB004C, (B) DIB004G and (C) co-culture of both strains, for all substrates product concentration is significantly increased in the co-culture compared to both individual cultures.

Figure 2:
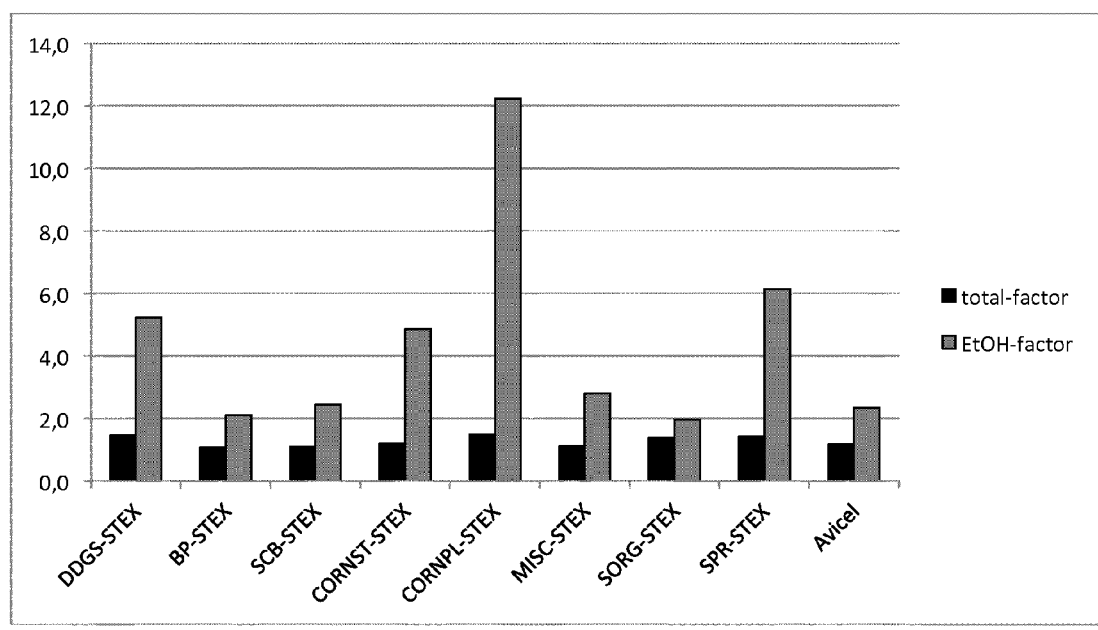
FIG. 2 shows a bar graph displaying the factorial increases in total product formation and ethanol formation comparing the hydrolytic strain *Caldicellulosiruptor* DIB004C and the co-culture of this strain with *Thermoanaerobacter* DIB004G.

FIG. 2 shows the factorial change in overall product formation in between culture of DIB004C alone and the co-culture of DIB004C with DIB004G. As well as in FIG. 1 it is clearly displayed that not only total product formation is increased but furthermore that ethanol formation is over proportionally increased compared to both individual cultures.

Example 5: Fermenter Batch Experiments

Batch experiments with e.g. DIB004C as well as with co-cultures of DIB004C and DIB004G were performed by cultivation on the medium described above with addition of 20 g/L poplar wood pretreated by "$SO_2$ steam explosion" comprising heating in the presence of dilute acid followed by sudden release of pressure.

Temperature is controlled to 72° C. and the pH-value is controlled to 6.5±0.25 throughout the fermentation. The fermenter is purged with nitrogen to remove excess oxygen before sodium sulphide is added as described above.

The fermentation is started by addition of a seed culture prepared as described in example 1.

The results of the HPLC analysis as described in example 2 show parallel production of ethanol, lactic acid and acetic acid with ethanol being the predominant product and acetate being produced only in a minor proportion.

Figure 3:
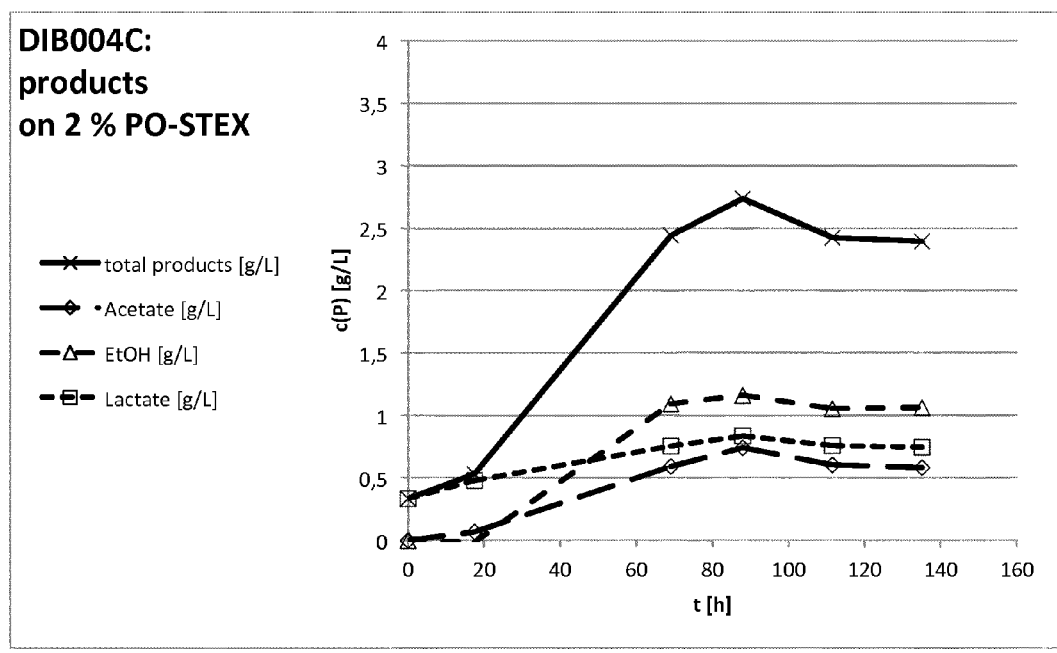
FIG. 3 is a diagram showing the product formation during growth of *Caldicellulosiruptor* sp. DIB004C on 20 g/L dry weight concentration of poplar wood pretreated by steam explosion (PO-STEX)

The results of the product formation during a fermentation of *Caldicellulosiruptor* sp. DIB004C on pretreated poplar wood is shown in FIG. 3.

Figure 4:
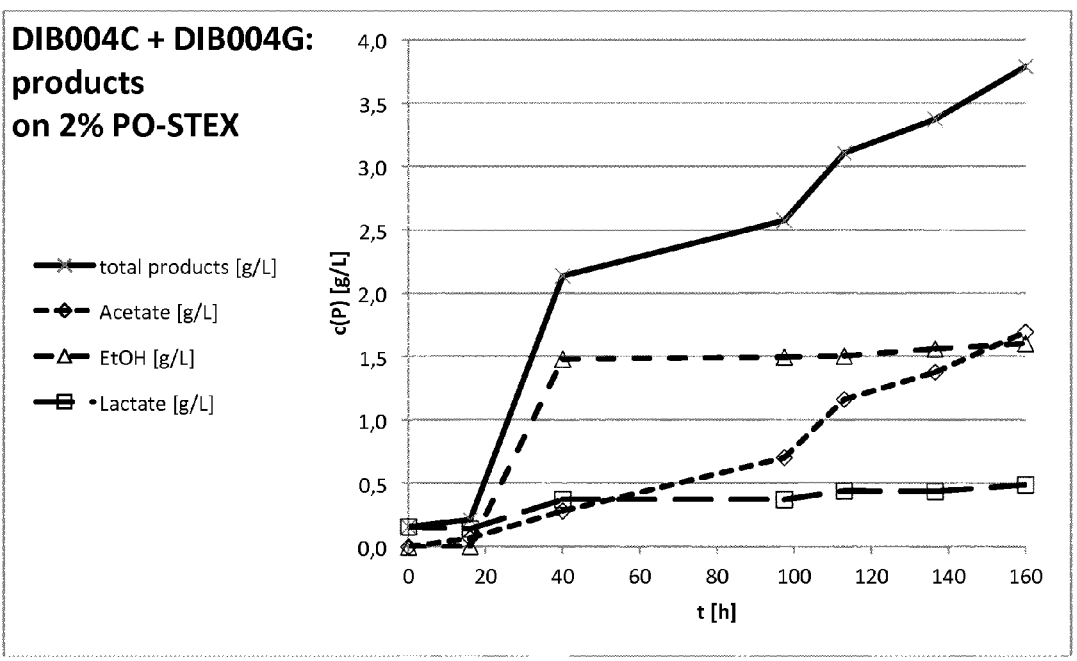
FIG. 4 is a diagram showing the product formation during growth of a co-culture comprising *Caldicellulosiruptor* sp. DIB004C and *Thermoanaerobacter* sp. DIB004G on 20 g/L dry weight concentration of poplar wood pretreated by steam explosion (PO-STEX)

FIG. 4 shows an identical fermentation approach applying a co-culture of *Caldicellulosiruptor* sp. DIB004C and *Thermoanaerobacter* sp. DIB004G.

Figure 5:
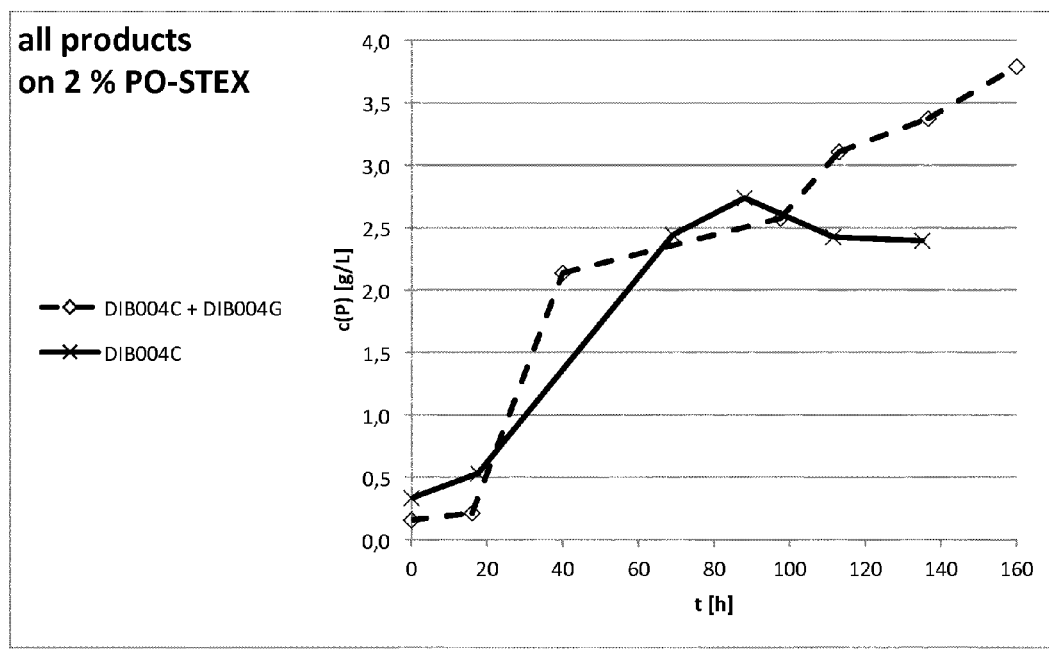
FIG. 5 is a diagram showing a direct comparison of total product formation in between *Caldicellulosiruptor* sp. DIB004C alone and a co-culture of *Caldicellulosiruptor* sp. DIB004 with *Thermoanaerobacter* sp. DIB004G on 20 g/L dry weight concentration of poplar wood pretreated by steam explosion (PO-STEX)

FIG. 5 shows a direct comparison in between total product concentration (ethanol+lactate+acetate) during both fermentation runs. It is clearly displayed that product formation during fermentation of both strains is both more rapid and enduring for a longer period of time. This is a clear indication for a synergistic effect of the both cultures leading to an overall increased product formation. A possible explanation for this synergistic effect would be that the strain *Thermoanaerobacter* sp. DIB004G would consume soluble sugar species more rapidly than the *Caldicellulosiruptor* strain leading to an improved de-repression of cellulolytic enzymes.

Example 6: Phylogeny

Figure 6:
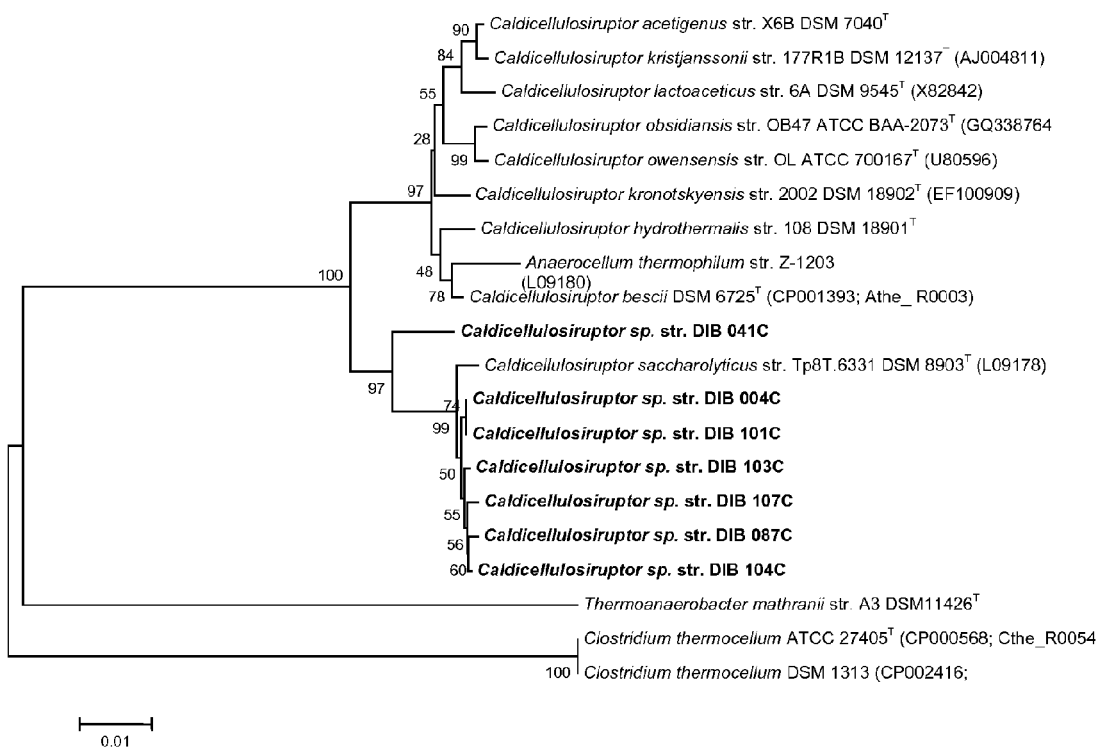
FIG. 6 illustrates a neighbor-joining tree based on 16S rRNA gene sequence comparisons of isolated *Caldicellulosiruptor* sp. strains and selected bacteria. Bootstrap values were based on 1,000 replicates. The scale bar represents 0.01 change per nucleotide position. GenBank accession numbers are given in parentheses. T, type strain.
Figure 7:
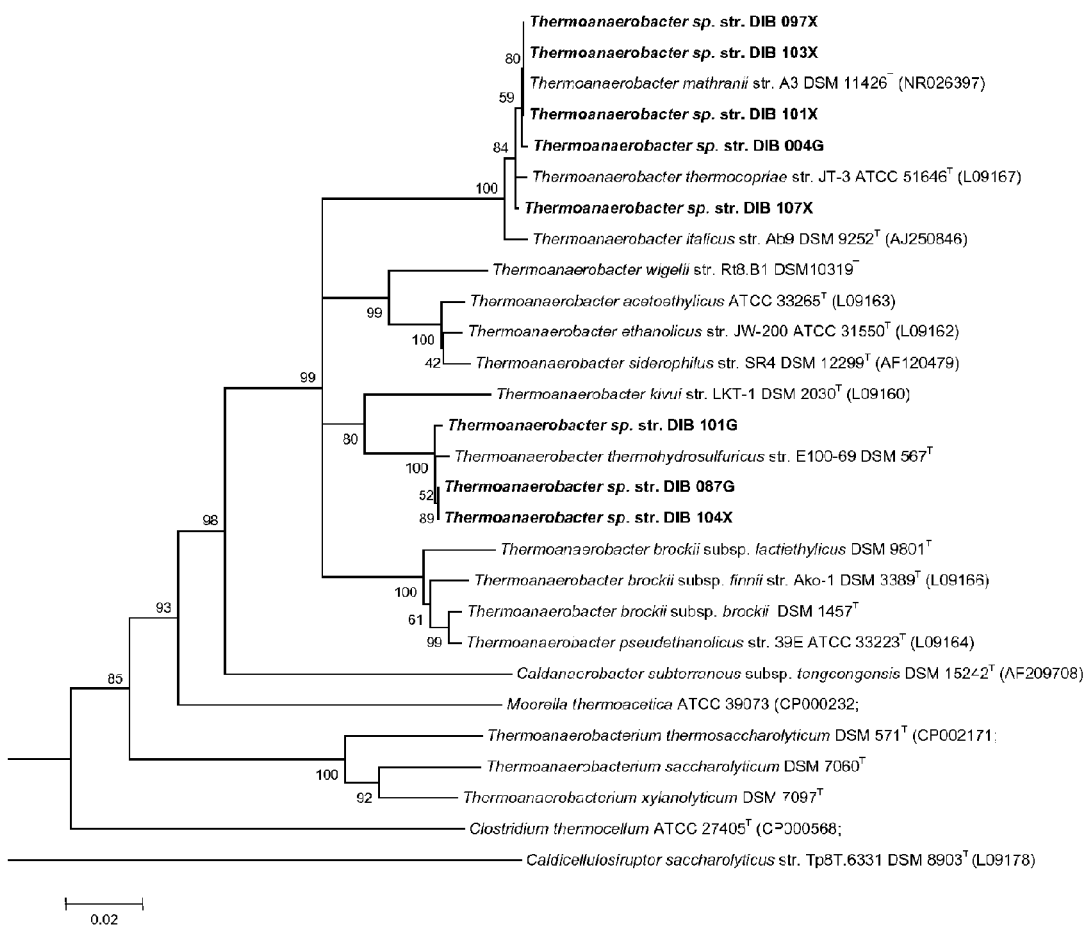
FIG. 7 illustrates a neighbor-joining tree based on 16S rRNA gene sequence comparisons of isolated *Thermoanaerobacter* sp. strains and selected bacteria. Bootstrap values were based on 1,000 replicates. The scale bar represents 0.01 change per nucleotide position. GenBank accession numbers are given in parentheses. T, type strain.

Sequencing of 16S rDNA from *Caldicellulosiruptor* strains listed in table 1 revealed that all of these strains had (at least) one copy of a 16S rDNA operon which was most closely related to *Caldicellulosiruptor saccharolyticus* strain Tp8T (DSM 8903) in the available public databases (FIG. 6).

Sequencing of 16S rDNA from *Thermoanaerobacter* sp. strains listed in table 2 revealed that all *Thermoanaerobacter* sp. strains had (at least) one copy of a 16S rDNA operon. Based on 16S rRNA sequences the *Thermoanaerobacter* sp. strains DIB004G, DIB097X, DIB101X, DIB103X and DIB107X were most closely related to *Thermoanaerobacter mathranii* strain A3 (DSM 11426) whereas the *Thermoanaerobacter* sp. strains DIB087G, DIB101G and DIB104X were most closely related to *Thermoanaerobacter thermohydrosulfuricus* strain E100-69 (DSM 567). Alignments were carried out using ClustalW (Chenna et al. 2003) and the phylogenetic tree was constructed by the neighbor-joining method (Saitou and Nei 1987) using the program MEGA 4 (Tamura et al. 2007).

LIST OF ADDITIONAL REFERENCES

Cayol J L, Ollivier B, Patel B K C, Ravot M, Magot M, Ageron E, Grimont P A D, Garcia J L. (1995) Description of *Thermoanaerobacter brockii* subsp. *lactiethylicus* subsp. nov., isolated from a deep subsurface french oil well. a proposal to reclassify *Thermoanaerobacter finnii* as *Thermoanaerobacter brockii* subsp. *finnii* comb. nov., and an emended description of *Thermoanaerobacter brockii*. Int J Syst Bacteriol 45:783-789.

Chenna R, Sugawara H, Koike T, Lopez R, Gibson T J, Higgins D G, Thompson J D. (2003) Multiple sequence alignment with the Clustal series of programs. Nucleic Acids Res 13:3497-3500.

Donnison A M, Brockelsby C M, Morgan H W, Daniel R M. (1989) The degradation of lignocellulosics by extremely thermophilic microorganisms. Biotechnol Bioeng 33:1495-1499.

Hungate R E. (1969) A roll tube method for cultivation of strict anaerobes. In: Methods in Microbiology Eds. Norris J R and Ribbons D W. pp 118-132. New York: Academic Press.

Larsen L, Nielsen P, Ahring B K. (1997) *Thermoanaerobacter mathranii* sp. nov., an ethanol-producing, extremely thermophilic anaerobic bacterium from a hot spring in Iceland. Arch Microbiol 168:114-119.

Lee Y-E, Jain M K, Lee c. Lowe S E, Zeikus J G (1993) Taxonomic distinction of saccharolytic thermophilic anaerobes: Description of *Thermoanaerobacterium xylanolyticum* gen. nov., sp. nov., and *Thermoanaerobacterium saccharolyticum* gen. nov., sp. nov.; Reclassification of *Thermoanaerobium brockii*, *Clostridium thermosulfurogenes*, and *Clostridium thermohydrosulfiricum* E100-69 as *Thermoanaerobacter brockii* comb. nov., *Thermoanaerobacterium thermosulfurigenes* comb. nov., and *Thermoanaerobacter thermohydrosulfuricus* comb. nov., respectively; and transfer of *Clostridium hermohydrosulfuricum* 39E to *Thermoanaerobacter ethanolicus*. Int J Syst Bacteriol 43:41-51.

Rainey F A, Donnison A M, Janssen P H, Saul D, Rodrigo A, Bergquist P L, Daniel R M, Stackebrandt E, Morgan H W. (1994) Description of *Caldicellulosiruptor saccharolyticus* gen. nov., sp. nov: an obligately anaerobic, extremely thermophilic, cellulolytic bacterium. FEMS Microbiol Lett 120:263-266.

Saitou N, Nei M (1987) The neighbor-joining method: a new method for reconstructing phylogenetic trees. Mol Biol Evol 4:406-425.

Sissons C H, Sharrock K R, Daniel R M, Morgan H W. (1987) Isolation of cellulolytic anaerobic extreme thermophiles from New Zealand thermal sites. Appl Environ Microbiol. 53:832-838.

Tamura K, Dudley J, Nei M, Kumar S (2007) MEGA4: Molecular Evolutionary Genetics Analysis (MEGA) software version 4.0. Mol Biol Evol 24:1596-1599.

U.S. Pat. No. 6,555,350
International patent application WO 2007/134607
International patent application WO 2010/075213
International patent application WO 2009/108908

What is claimed is:

1. A method for converting lignocellulosic biomass to a biofuel and/or another carbon-based product, comprising the step of contacting the lignocellulosic biomass with a microbial co-culture for a period of time at an initial temperature and an initial pH, thereby producing an amount of a biofuel and/or other carbon-based chemicals, wherein the microbial co-culture comprises a first microorganism belonging to the genus *Caldicellulosiruptor* and a second microorganism belonging to the genus *Thermoanaerobacter*, further wherein:
   a) the first microorganism is selected from the group consisting of DIB004C deposited as DSM 25177, DIB101C deposited as DSM 25178, DIB041C deposited as DSM 25771, DIB087C deposited as DSM25772, DIB103C deposited as DSM 25773, DIB104C deposited as DSM 25774 and DIB107C deposited as DSM 25775, and
   b) the second microorganism is selected from the group consisting of DIB004G deposited as DSM 25179, DIB101G deposited as DSM 25180, DIB101X deposited as DSM 25181, DIB097X deposited as DSM 25308, DIB087G deposited as DSM 25777, DIB103X deposited as DSM 25776, DIB 104X deposited as DSM 25778 and DIB 107X deposited as DSM 25779.

2. The method according to claim 1, wherein the period of time is 10 h to 300 h, optionally 50 h to 200 h or 80 h to 160 h.

3. The method according to claim 1, wherein the initial temperature is in the range between 55° C. and 80° C., optionally between 72° C. and 78° C.

4. The method according to claim 1, wherein the initial pH is between 5 and 9, optionally between 6 and 8.

5. The method according to claim 1, wherein the biofuel is an alcohol, optionally ethanol.

6. The method according to claim 1, wherein the carbon-based product is a carboxylic acid, optionally lactic acid or a salt or ester thereof.

7. The method according to claim 1, wherein the lignocellulosic biomass is selected from the group consisting of grass, switch grass, cord grass, rye grass, reed canary grass, mixed prairie grass, *miscanthus*, sugar-methoding residues, sugarcane bagasse, sugarcane straw, agricultural wastes, rice straw, rice hulls, barley straw, corn cobs, cereal straw, wheat straw, canola straw, oat straw, oat hulls, corn fiber, corn stover, soybean stover, corn stover, forestry wastes, recycled wood pulp fiber, paper sludge, sawdust, hardwood, softwood, pressmud from sugar beet, cotton stalk, banana leaves, residues from vegetable oil production and lignocellulosic biomass material obtained through processing of food plants.

8. The method according to according to claim 1, wherein said lignocellulosic biomass is a pretreated lignocellulosic biomass derived from a mechanical, thermochemical, and/or biochemical pretreatment.

9. The method according to according to claim 8, wherein pretreating the lignocellulosic biomass material comprises exposing the lignocellulosic biomass to steam treatment.

10. The method according to according to claim 8, wherein pretreating the lignocellulosic biomass material comprises exposing the lignocellulosic biomass to steam treatment and enzymatic treatment, optionally with cellulose and/or hemicellulose degrading enzymes.

11. The method according to claim 8, wherein pretreating the lignocellulosic biomass material comprises mechanical comminution and a subsequent treatment with sulfuric acid, sulfurous acid or their respective anhydrides under heat and pressure with or without a sudden release of pressure.

12. The method according to claim 8, wherein pretreating the lignocellulosic biomass material comprises mechanical comminution and a subsequent treatment with ammonia hydroxide, sodium hydroxide, potassium hydroxide or calcium hydroxide or, as far as applicable, their respective anhydrides, under heat and pressure with or without a sudden release of pressure.

13. The method according to claim 1, further comprising separating and recovering the converted biofuel and/or the carbon-based chemical from the residual biomass and culture.

* * * * *

SEQUENCE LISTING

```
<160> NUMBER OF SEQ ID NOS: 17

<210> SEQ ID NO 1
<211> LENGTH: 1396
<212> TYPE: DNA
<213> ORGANISM: Artificial Sequence
<220> FEATURE:
<223> OTHER INFORMATION: 16SrDNA from Caldicellulosiruptor sp. DIB004C

<400> SEQUENCE: 1
ttacgacttc accccaatca tcagccccac cttcaacaca gcttaacctg tgtcttcagg      60
tgttgctgac tctcatggtg tgacgggcgg tgtgtacaag gcccgggaac gtattcaccg     120
cggcatgctg atccgcgatt actagcgatt ccgacttcat gcaggcgagt tgcagcctgc     180
aatccgaact gggggtgctt ttttgggatt cgctccggct cgcgccttcg cacgccctct     240
gtagcaccca ttgtagcacg tgtgtagccc agggcataag gggcatgatg atttgacgtc     300
atccccacct tcctccgcct catcgacggc agtcccctta gagtgcccac cattacgcgc     360
```

| | |
|---|---|
| tggcaactaa gggcaggggt tgcgctcgtt gcgggactta acccaacatc tcacgacacg | 420 |
| agctgacgac aaccatgcac cacctgtgtc cgggctcctg ctctcatcga acaggcaccc | 480 |
| caccctttcg ggcaggtccc cggcatgtca agccctggta aggttcttcg cgttgcttcg | 540 |
| aattaaacca catgctccac cgcttgtgcg ggccccgtc aattcctttg agtttcaacc | 600 |
| ttgcggccgt actccccagg cgggatgctt attgtgttaa ctacggcacg gaggagtcct | 660 |
| tctcccccac acctagcatc catcgtttac agcgtggact accagggtat ctaatcctgt | 720 |
| tcgctcccca cgctttcgtg cctcagcgtc agttacggtc cagacggccg ccttcgccac | 780 |
| tggtgttcct cccgatatct acgcatttca ccgctacacc gggaattccg ccgtcctctc | 840 |
| ccgcactcaa gctatgcagt attaagcgca atccttaggt tgagcctaag gctttcacgc | 900 |
| ttaactcgca tagccgccta cgcaccctt acgcccagta attccggaca acgctcgcca | 960 |
| cctacgtatt accgcggctg ctggcacgta gttagccgtg gcttttttaaa cgggtactat | 1020 |
| ctcctacttc tccccgtcca aagaggttta caccccgaag ggcttcttcc ctcacgcggc | 1080 |
| gtcgctgcgt caggcttccg cccattgcgc aagattcccc gctgctgcct cccgtaggag | 1140 |
| tgtgggccgt gtctcagtcc cactgtggcc gtacaccctc tcaggccggc tacccgtcgt | 1200 |
| cgccttggta ggccgttacc ccaccaacta gctgatgggc cgcgagccca tccccagcca | 1260 |
| gtatagcctc cccggctacc ctttcaccac atcaccatgc gatgacgtgg tcccatcggg | 1320 |
| tattagcagc cctttcgagc tgttatcccc gtgctggggg taggttgctc acgtgttact | 1380 |
| cacccgtccg ccgcta | 1396 |

<210> SEQ ID NO 2
<211> LENGTH: 1480
<212> TYPE: DNA
<213> ORGANISM: Artificial Sequence
<220> FEATURE:
<223> OTHER INFORMATION: 16SrDNA from Caldicellulosiruptor sp. DIB041C

<400> SEQUENCE: 2

| | |
|---|---|
| ctcaggacga acgctggcgg cgtgcctaac gcatgcaagt cgagcggagg tagccatgaa | 60 |
| ggtgaagagc tggagtggct atcttagcgg cggacgggtg agtaacacgt gagcaaccta | 120 |
| ccctcagcac ggggataaca gctcgaaagg ctgctaata cccgatggga ccacggcatc | 180 |
| gcatgatgtt gtggtgaaag ggtagccgtg gaggctatac cggctgggga tgggctcgcg | 240 |
| gcccatcagc tagttggtgg ggtaacggcc taccaaggct acgacgggta gccggcctga | 300 |
| gagggtggtc ggccacagtg ggactgagac acggcccaca ctcctacggg aggcagcagc | 360 |
| ggggaatctt gcgcaatggg cgaaagcctg acgcagcgac gccgcgtgag ggaggaagcc | 420 |
| cttcggggtg taaaccctctt tggacgggga gaaggaggag atagtacccg tttaaaaagc | 480 |
| cacggctaac tacgtgccag cagccgcggt aatacgtagg tggcgagcgt tgtccggaat | 540 |
| tactgggcgt aaagggtgcg taggcggcta tgcaagttaa gcgtgaaatc ttggggctca | 600 |
| accccaaggc tgcgcttaat actgcatagc ttgagtgcgg gagaggacgg cggaattccc | 660 |
| ggtgtagcgg tgaaatgcgt agatatcggg aggaacacca gtggcgaagg cggccgtctg | 720 |
| gaccgtaact gacgctgagg cacgaaagcg tgggagcga acaggattag ataccctggt | 780 |
| agtccacgct gtaaacgatg gatgctaggt gtggggggaga aggactcctc cgtgccgtag | 840 |
| ttaacacaat aagcatcccg cctggggagt acggccgcaa ggttgaaact caaaggaatt | 900 |
| gacggggggcc cgcacaagcg gtggagcatg tggtttaatt cgaagcaacg cgaagaacct | 960 |
| taccagggct tgacatgccg ggaacctgcc cgaaagggtg gggtgcctgc gcgatgagtg | 1020 |

```
caggagcccg acacaggtg gtgcatggtt gtcgtcagct cgtgtcgtga gatgttgggt    1080
taagtcccgc aacgagcgca acccctgccc ttagttgcca gcacgtaatg gtgggcactc    1140 taagggact gccgccgatg aggcggagga aggtggggat gacgtcaaat catcatgccc     1200
cttatgccct gggctacaca cgtgctacaa tgggtgctac agagggttgc gaaggcgcga    1260
gccggagcta atcccaaaaa agcaccccca gttcggattg caggctgcaa ctcgcctgca    1320
tgaagtcgga atcgctagta atcgcggatc agcatgccgc ggtgaatacg ttcccgggcc    1380
ttgtacacac cgcccgtcac accatgagag tcagcaacac ctgaagacac agggcagctg    1440
tgttgaaggt ggggctgatg attggggtga agtcgtaaca                          1480
```

<210> SEQ ID NO 3
<211> LENGTH: 1481
<212> TYPE: DNA
<213> ORGANISM: Artificial Sequence
<220> FEATURE:
<223> OTHER INFORMATION: 16SrDNA from Caldicellulosiruptor sp. DIB087C

<400> SEQUENCE: 3

```
tcaggacgaa cgctggcggc gtgcctaacg catgcaagtc gagcggagat ggtggttgaa    60
ggtgatgagc tggaggctgc catcttagcg gcggacgggt gagtaacacg tgagcaacct    120 accccagca cggggataac agctcgaaag ggctgctaat accgatgggg accacgtcat     180
cgcatggtga tgtggtgaaa gggtagccgg ggaggctata ctggctgggg atgggctcgc    240
ggcccatcag ctagttggtg gggtaacggc tcaccaaggc gacgacgggt agccggcctg    300
agagggtgta cggccacagt gggactgaga cacgcccac actcctacgg gaggcagcag    360
cggggaatct tgcgcaatgg gcggaagcct gacgcagcga cgccgcgtga gggaagaagc    420
ccttcggggt gtaaacctct ttggacgggg agaagtagga gatagtaccc gtttaaaaag   480
ccacggctaa ctacgtgcca gcagccgcgg taatacgtag gtggcgagcg ttgtccggaa    540
ttactgggcg taaagggtgc gtaggcggct atgcgagtta agcgtgaaag ccttaggctc    600
aacctaagga ttgcgcttaa tactgcatag cttgagtgcg ggagaggacg gcggaattcc    660
cggtgtagcg gtgaaatgcg tagatatcgg gaggaacacc agtggcgaag gcggccgtct    720
ggaccgtaac tgacgctgag gcacgaaagc gtggggagcg aacaggatta gataccctgg    780
tagtccacgc tgtaaacgat ggatgctagg tgtggggag aaggactctt ccgtgccgta    840
gttaacacaa taagcatccc gcctgggag tacggccgca aggttgaaac tcaaaggaat    900 tgacggggc cgcacaagc ggtggagcat gtggtttaat tcgaagcaac gcgaagaacc     960
ttaccagggc ttgacatgcc ggggacctgc ccgaaagggt ggggtgcctg ttcgatgaga    1020
gcaggaaccc ggacacaggt ggtgcatggt tgtcgtcagc tcgtgtcgtg agatgttggg    1080
ttaagtcccg caacgagcgc aacccctgcc cttagttgcc agcgggtaat ggtgggcact    1140 ctaagggac tgccgtcgat gaggcggagg aaggtgggga tgacgtcaaa tcatcatgcc    1200
ccttatgccc tgggctacac acgtgctaca atgggtgcta cagagggcgt gcgaaggcgc    1260
gagccggagc gaatcccaaa aaagcacccc cagttcggat tgcaggctgc aactcgcctg    1320
catgaagtcg gaatcgctag taatcgcgga tcagcatgcc gcggtgaata cgttcccggg    1380
ccttgtacac accgcccgtc acaccatgag agtcagcaac acctgaagac acaggttaag    1440
ctgtgttgaa ggtggggctg atgattgggg tgaagtcgta a                        1481
```

<210> SEQ ID NO 4

<211> LENGTH: 1212
<212> TYPE: DNA
<213> ORGANISM: Artificial Sequence
<220> FEATURE:
<223> OTHER INFORMATION: 16SrDNA from Caldicellulosiruptor sp. DIB101C

<400> SEQUENCE: 4

```
cctgtgtctt caggtgttgc tgactctcat ggtgtgacgg gcggtgtgta caaggcccgg      60
gaacgtattc accgcggcat gctgatccgc gattactagc gattccgact tcatgcaggc     120
gagttgcagc ctgcaatccg aactgggggt gcttttttgg gattcgctcc ggctcgcgcc     180
ttcgcacgcc ctctgtagca cccattgtag cacgtgtgta gcccagggca taaggggcat     240
gatgatttga cgtcatcccc accttcctcc gcctcatcga cggcagtccc cttagagtgc     300
ccaccattac gcgctggcaa ctaagggcag gggttgcgct cgttgcggga cttaacccaa     360
catctcacga cacgagctga cgacaaccat gcaccacctg tgtccgggct cctgctctca     420
tcgaacaggc accccaccct ttcgggcagg tccccggcat gtcaagccct ggtaaggttc     480
ttcgcgttgc ttcgaattaa accacatgct ccaccgcttg tgcgggcccc cgtcaattcc     540
tttgagtttc aaccttgcgg ccgtactccc caggcgggat gcttattgtg ttaactacgg     600
cacggaggag tccttctccc ccacacctag catccatcgt ttacacgtg gactaccagg     660
gtatctaatc ctgttcgctc cccacgcttt cgtgcctcag cgtcagttac ggtccagacg     720
gccgccttcg ccactggtgt tcctcccgat atctacgcat ttcaccgcta caccgggaat     780
tccgccgtcc tctcccgcac tcaagctatg cagtattaag cgcaatcctt aggttgagcc     840
taaggctttc acgcttaact cgcatagccg cctacgcacc ctttacgccc agtaattccg     900
gacaacgctc gccacctacg tattaccgcg gctgctggca cgtagttagc cgtggctttt     960
taaacgggta ctatctccta cttctccccg tccaaagagg tttacacccc gaagggcttc    1020
ttccctcacg cggcgtcgct gcgtcaggct tccgcccatt gcgcaagatt ccccgctgct    1080
gcctcccgta ggagtgtggg ccgtgtctca gtcccactgt ggccgtacac cctctcaggc    1140
cggctacccg tcgtcgcctt ggtaggccgt tacccaccca actagctgat gggccgcgag    1200
cccatcccca gc                                                        1212
```

<210> SEQ ID NO 5
<211> LENGTH: 1253
<212> TYPE: DNA
<213> ORGANISM: Artificial Sequence
<220> FEATURE:
<223> OTHER INFORMATION: 16SrDNA from Caldicellulosiruptor sp. DIB103C

<400> SEQUENCE: 5

```
cgacttcacc ccaatcatca gccccacctt caacacagct taacctgtgt cttcaggtgt      60
tgctgactct catggtgtga cgggcggtgt gtacaaggcc cgggaacgta ttcaccgcgg     120
catgctgatc cgcgattact agcgattccg acttcatgca ggcgagttgc agcctgcaat     180
ccgaactggg ggtgcttttt tgggattcgc tccggctcgc gccttcgcac gccctctgta     240
gcacccattg tagcacgtgt gtagcccagg gcataagggg catgatgatt tgacgtcatc     300
cccaccttcc tccgcctcat cgacggcagt cccctttagag tgcccaccat tacgcgctgg     360
caactaaggg caggggttgc gctcgttgcg ggacttaacc caacatctca cgacacgagc     420
tgacgacaac catgcaccac ctgtgtccgg gctcctgctc tcatcgaaca ggcaccccac     480
cctttcgggc aggtccccgg catgtcaagc cctggtaagg ttcttcgcgt tgcttcgaat     540
taaaccacat gctccaccgc ttgtgcgggc ccccgtcaat tcctttgagt ttcaaccttg     600
```

```
cggccgtact ccccaggcgg gatgcttatt gtgttaacta cggcacggag gagtccttct      660
cccccacacc tagcatccat cgtttacagc gtggactacc agggtatcta atcctgttcg      720
ctccccacgc tttcgtgcct cagcgtcagt tacggtccag acggccgcct tcgccactgg      780
tgttcctccc gatatctacg catttcaccg ctacaccggg aattccgccg tcctctcccg      840
cactcaagct atgcagtatt aagcgcaatc cttaggttga gcctaaggct ttcacgctta      900
actcgcatag ccgcctacgc acccttacgc cccagtaatt ccggacaacg ctcgccacct      960
acgtattacc gcggctgctg gcacgtagtt agccgtggct ttttaaacgg gtactatctc     1020
ctacttctcc ccgtccaaag aggtttacac cccgaagggc ttcttccctc acgcggcgtc     1080
gctgcgtcag gcttccgccc attgcgcaag attccccgct gctgcctccc gtaggagtgt     1140
gggccgtgtc tcagtcccac tgtggccgta caccctctca ggccggctac ccgtcgtcgc     1200
cttggtaagc cgttacccca ccaactagct gatgggccgc gagcccatcc cca            1253
```

<210> SEQ ID NO 6
<211> LENGTH: 1255
<212> TYPE: DNA
<213> ORGANISM: Artificial Sequence
<220> FEATURE:
<223> OTHER INFORMATION: 16SrDNA from Caldicellulosiruptor sp. DIB104C

<400> SEQUENCE: 6

```
gacttcaccc caatcatcag ccccaccttc aacacagctt aacctgtgtc ttcaggtgtt       60
gctgactctc atggtgtgac gggcggtgtg tacaaggccc gggaacgtat tcaccgcggc      120
atgctgatcc gcgattacta gcgattccga cttcatgcag gcgagttgca gcctgcaatc      180
cgaactgggg gtgcttttt gggattcgct ccggctcgcg ccttcgcacg ccctctgtag      240
cacccattgt agcccgtgtg tagcccaggg cataagggc atgatgattt gacgtcatcc      300
ccaccttcct ccgcctcatc gacggcagtc cccttagagt gcccaccatt acgcgctggc      360
aactaagggc aggggttgcg ctcgttgcgg gacttaaccc aacatctcac gacacgagct      420
gacgacaacc atgcaccacc tgtgtccggg ctcctgctct catcgaacag gcaccccacc      480
ctttcgggca ggtccccggc atgtcaagcc ctggtaaggt tcttgcgtt gcttcgaatt      540 aaaccacatg ctccaccgct tgtgcgggcc ccgtcaatt cctttgagtt tcaaccttgc      600
ggccgtactc cccaggcggg atgcttattg tgttaactac ggcacggaag agtccttctc      660
ccccacacct agcatccatc gtttacagcg tggactacca gggtatctaa tcctgttcgc      720
tccccacgct ttcgtgcctc agcgtcagtt acggtccaga cggccgcctt cgccactggt      780
gttcctcccg atatctacgc atttcaccgc tacaccggga attccgccgt cctctcccgc      840
actcaagcta tgcagtatta agcgcaatcc ttaggttgag cctaaggctt tcacgcttaa      900
ctcgcatagc cgcctacgca cccttacgcc cagtaattcg gacaacgc tcgccaccta      960 cgtattaccg cggctgctgg cacgtagtta gccgtggctt tttaaacggg tactatctcc     1020
tacttctccc cgtccaaaga ggtttacacc ccgaagggct tcttccctca cgcggcgtcg     1080
ctgcgtcagg cttccgccca ttgcgcaaga ttccccgctg ctgcctcccg taggagtgtg     1140
ggccgtgtct cagtcccact gtggccgtac accctctcag gccggctacc cgtcgtcgcc     1200
ttggtgagcc gttacccac caactagctg atgggccgcg agcccatccc cagcc           1255
```

<210> SEQ ID NO 7
<211> LENGTH: 1466
<212> TYPE: DNA

<213> ORGANISM: Artificial Sequence
<220> FEATURE:
<223> OTHER INFORMATION: 16SrDNA from Caldicellulosiruptor sp. DIB107C

<400> SEQUENCE: 7

```
gacttcaccc ccaatcatca gccccacctt caacacagct taacctgtgt cttcaggtgt      60
tgctgactct catggtgtga cgggcggtgt gtacaaggcc cgggaacgta ttcaccgcgg     120
catgctgatc cgcgattact agcgattccg acttcatgca ggcgagttgc agcctgcaat     180
ccgaactggg ggtgcttttt tgggattcgc tccggctcgc gccttcgcac gccctctgta     240
gcacccattg tagcacgtgt gtagcccagg cataagggg catgatgatt tgacgtcatc      300
cccaccttcc tccgcctcat cgacggcagt ccccttagag tgcccaccat tacgcgctgg     360
caactaaggg cagggggttgc gctcgttgcg ggacttaacc caacatctca cgacacgagc    420
tgacgacaac catgcaccac ctgtgtccgg gctcctgctc tcatcgaaca ggcacccac     480
cctttcgggc aggtccccgg catgtcaagc cctggtaagg ttcttcgcgt tgcttcgaat     540
taaaccacat gctccaccgc ttgtgcgggc ccccgtcaat tcctttgagt ttcaaccttg    600
cggccgtact ccccaggcgg gatgcttatt gtgttaacta cggcacggag gagtccttct    660
cccccacacc tagcatccat cgtttacagc gtggactacc agggtatcta atcctgttcg    720
ctccccacgc tttcgtgcct cagcgtcagt tacggtccag acggccgcct tcgccactgg    780
tgttcctccc gatatctacg catttcaccg ctacaccggg aattccgccg tcctctcccg    840
cactcaagct atgcagtatt aagcgcaatc cttaggttga gcctaaggct ttcacgctta    900
actcgcatag ccgcctacgc accctttacg cccagtaatt ccggacaacg ctcgccacct   960
acgtattacc gcggctgctg gcacgtagtt agccgtggct ttttaaacgg gtactatctc   1020
ctacttctcc ccgtccaaag aggtttacac cccgaagggc ttcttccctc acgcggcgtc   1080
gctgcgtcag gcttccgccc attgcgcaag attccccgct gctgcctccc gtaggagtgt   1140
gggccgtgtc tcagtcccac tgtggccgta caccctctca ggccggctac ccgtcgtcgc   1200
cttggtgagc cgttacctca ccaactagct gatgggccgc gagcccatcc ccagccggat   1260
tactcctttc accacatcac catgcgatga cgtggtccca tcgggtatta gcagcccttt   1320
cgagctgtta tccccgtgct gggggtaggt tgctcacgtg ttactcaccc gtccgccgct   1380
aagatggcag cctccagctc atcaccttca accaccatct ccgctcgact tgcatgcgtt   1440
aggcacgccg ccagcgttcg tcctga                                          1466
```

<210> SEQ ID NO 8
<211> LENGTH: 1422
<212> TYPE: DNA
<213> ORGANISM: Artificial Sequence
<220> FEATURE:
<223> OTHER INFORMATION: 16SrDNA from Thermoanaerobacter sp. DIB004G

<400> SEQUENCE: 8

```
ggttgggtca ccggcttcgg gtgtcgcagg ctctcgtggt gtgacgggcg gtgtgtacaa      60
ggcccgggaa cgtattcacc gcggcatgct gatccgcgat tactagcgat tccgacttca    120
tgcaggcgag ttgcagcctg caatccgaac ttggaccggc ttttttgggat tcgctccgcc   180
tcacggcttc gcttccctct gtaccggcca ttgtagcacg tgtgtggccc agggcattta    240
gggcatgatg atttgacgtc atccccacct tcctccgtgt cctccacggc agtccctcta    300
gagtgcccgg cttacccgct ggcaactaga ggcaggggtt gcgctcgttg cgggacttaa    360
cccaacatct cacgacacga gctgacgaca accatgcacc acctgtgcag gctccttacc    420
```

```
tcccggtaag gtcgctcccc tttcggttcg ctactacctg catgtcaagc cctggtaagg      480
ttcttcgcgt tgcttcgaat taaaccacat gctccaccgc ttgtgcgggc ccccgtcaat      540
tcctttgagt ttcaaccttg cggccgtact ccccaggcgg ggtacttatt gcgttcgcta      600
cggcacggaa cgcttccgcg ccccacacct agtacccatc gtttacagcg tggactacca      660
gggtatctaa tcctgttcgc tccccacgct ttcgcgcctc agcgtcaggg ccagtccaga      720
gagtcgcctt cgccactggt attcctcccg atatctacgc atttcaccgc tacaccggga      780
attccactcc cctctcctgc cctctagcca atcagtttca gatgctaccc cccggttgag      840
cccgggtctt ttacacctga cttgattgac cgcctacgcg ccctttacgc ccagtaattc      900
cggacaacgc tcgcccccta cgtcttaccg cggctgctgg cacgtagtta gccggggctt      960
tcgtgtggta ccgtcatccc ttcttcccac actaacgggg tttacaaccc gaaggccttc     1020
ctcccccacg cggcgtcgct gggtcaggct tccgcccatt gcccaagatt ccccactgct     1080
gcctcccgta ggagtctggg ccgtgtctca gtcccagtgt ggccgtccac cctctcaggc     1140
cggctacccg tcgtcgcctt ggtaggccgt taccctacca actagctgat gggacgcggg     1200
cccatcctta agcggtagct tgcgcttccc tttcctccct ataggatgcc ctataaggag     1260
cttatccagt attaccaccc ctttcgaggt gctatcccgg tcttaagggt aggttgccca     1320
cgcgttactc acccgtccgc cgctatccgc cacccaacta cgttgagtgc cggaccgctc     1380
gactgcatgt gttaggcacg ccgccagcgt tcgtcctgag cc                        1422

<210> SEQ ID NO 9
<211> LENGTH: 1659
<212> TYPE: DNA
<213> ORGANISM: Artificial Sequence
<220> FEATURE:
<223> OTHER INFORMATION: 16SrDNA from Thermoanaerobacter sp. DIB087G

<400> SEQUENCE: 9
actcaagtgg gcacgttttt ttctcttcat cacgtttcta acatgcccac ttgagtgccg       60
ggttgggtca ccggcttcgg gtgttgcaga ctctcgtggt gtgacgggcg gtgtgtacaa      120
ggcccgggaa cgtattcacc gcggcatgct gatccgcgat tactagcgat tccgacttca      180
tgcaggcgag ttgcagcctg caatccgaac ttggaccggc ttttggggt ccgctccaga      240 tcgctccttc gcctccctct gtaccggcca ttgtagcacg tgtgtggccc agggcatata      300
gggcatgatg atttgacgtc atccccacct tcctccgtgt tgtccacggc agtccctcta      360
gagtgcctcc gtcactcaac tgaacacgct atcccttcct ctctactctt tcctaacatg      420
ttcagttgag tgacggactg gcaactagaa gcaaggggttg cgctcgttgc gggacttaac      480
ccaacatctc acgacacgag ctgacgacaa ccatgcacca cctgtgcagg ctcccggcac      540
tcaagtaggc acttcattct ccctcttact accttctcta tcatgcccac ttgagtgccg      600
ggtcgctcac ctttcggctc gctactacct gcatgtcaag ccctggtaag gttcttcgcg      660
ttgcttcgaa ttaaaccaca tgctccaccg cttgtgcggg ccccgtcaa ttcctttgag      720 tttcaacctt gcggccgtac tccccaggcg gggtacttat tgcgttaact acggcacgga      780
atgcttccgc atcccacacc tagtacccat cgtttacggc gtggactacc agggtatcta      840
atcctgtttg ctccccacgc tttcgcgcct cagcgtcagg gtcagtccag agagtcgcct      900
tcgccactgg tattcctccc gatatctacg catttcaccg ctacaccggg aattccactc      960
ccctctcctg ccctctagcc acccagtttc atgtgcatcc ccgggttga gcccgggttt     1020
```

| | |
|---|---:|
| tttacacctg acttaagtgg ccgcctacgc gcccttttacg cccagtaatt ccggacaacg | 1080 |
| ctcgccccct acgtcttacc gcggctgctg gcacgtagtt agccggggct ttcgtgtggt | 1140 |
| accgtcatct attcttccca cactatcgag ctttacgacc cgaaggcctt cttcgctcac | 1200 |
| gcggcgtcgc tgcgtcaggc tttcgcccat tgcgcaagat tccccactgc tgcctcccgt | 1260 |
| aggagtctgg gccgtgtctc agtcccagtg tggccgacca ccctctcagg ccggctaccc | 1320 |
| gtcgtcgcct tggtaggccg ttaccctacc aactagctga tgggacgcgg gcccatcctt | 1380 |
| aagcggtagc ttccgctacc ttccctcctc ataggatgcc ctacaaggag cttatccagt | 1440 |
| attagcaccc ctttcgaggt gttatcccgg tcttaagggt aggttgccca cgcgttactc | 1500 |
| acccgtccgc cgctatccgg cactcaactc cgtgcttacc ttactttgca ccactttat | 1560 |
| tactttcttc ttctactata cttccttccc cttaagtaag cacttagttg agtgccggac | 1620 |
| cgctcgactt gcatgtgtta ggcacgccgc cagcgttcg | 1659 |

<210> SEQ ID NO 10
<211> LENGTH: 1436
<212> TYPE: DNA
<213> ORGANISM: Artificial Sequence
<220> FEATURE:
<223> OTHER INFORMATION: 16SrDNA from Thermoanaerobacter sp. DIB097X

<400> SEQUENCE: 10

| | |
|---|---:|
| cccggttggg tcaccggctt cgggtgtcgc aggctctcgt ggtgtgacgg gcggtgtgta | 60 |
| caaggcccgg gaacgtattc accgcggcat gctgatccgc gattactagc gattccgact | 120 |
| tcatgcaggc gagttgcagc ctgcaatccg aacttggacc ggcttttttgg gattcgctcc | 180 |
| gcctcgcggc ttcgctcccc tctgtaccgg ccattgtagc acgtgtgtgg cccagggcat | 240 |
| atagggcatg atgatttgac gtcatcccca ccttcctccg tgtcctccac ggcagtcccc | 300 |
| ctagagtgcc cggcttaccc gctggcaact agaggcaggg gttgcgctcg ttgcgggact | 360 |
| taacccaaca tctcacgaca cgagctgacg acaaccatgc accacctgtg caggctcctt | 420 |
| acctcccggt aaggtcgctc cccttttcggt tcgctactac ctgcatgtca agccctggta | 480 |
| aggttcttcg cgttgcttcg aattaaacca catgctccac cgcttgtgcg ggccccgtc | 540 |
| aattcctttg agtttcaacc ttgcggccgt actccccagg cggggtactt attgcgttcg | 600 |
| ctacggcacg gaacgcttcc gcgcccccaca cctagtaccc atcgtttaca gcgtggacta | 660 |
| ccagggtatc taatcctgtt cgctccccac gctttcgcgc ctcagcgtca gggccagtcc | 720 |
| agagagtcgc cttcgccact ggtattcctc ccgatatcta cgcatttcac cgctacaccg | 780 |
| ggaattccac tccctctcc tgccctctag ccaatcagtt tcagatgcta ccccgggtt | 840 |
| gagcccgggt cttttacacc tgacttgatt gaccgcctac gcgcccttta cgcccagtaa | 900 |
| ttccggacaa cgctcgcccc ctacgtctta ccgcggctgc tggcacgtag ttagccgggg | 960 |
| ctttcgtgtg gtaccgtcat cccttcttcc cacactaacg gggtttacaa cccgaaggcc | 1020 |
| ttcctccccc acgcggcgtc gctgggtcag gcttccgccc attgcccaag attccccact | 1080 |
| gctgcctccc gtaggagtct gggccgtgtc tcagtcccag tgtggccgac caccctctca | 1140 |
| ggccggctac ccgtcgtcgc cttggtaggc cgttacccta ccaactagct gatgggacgc | 1200 |
| gggcccatcc ttaagcggta gcttgcgcct cccttttcctc cctataggat gccctataag | 1260 |
| gagcttatcc agtattacca ccccttttcga ggtgctatcc cggtcttaag ggtaggttgc | 1320 |
| ccacgcgtta ctcacccgtc cgccgctatc cgccacccaa ctacgttgag tgccggaccg | 1380 |
| ctcgacttgc atgtgttagg cacgccgcca gcgttcgtcc tgagccatga tcaaac | 1436 |

<210> SEQ ID NO 11
<211> LENGTH: 1080
<212> TYPE: DNA
<213> ORGANISM: Artificial Sequence
<220> FEATURE:
<223> OTHER INFORMATION: 16SrDNA from Thermoanaerobacter sp. DIB101G

<400> SEQUENCE: 11

```
gctcaggacg aacgctggcg gcgtgcctaa cacatgcaag tcgagcggtc cggcactcaa       60
ctaagtgctt acttaagggg aaggaagtat agtagaagaa gaaggtaata aaagtgatgc      120
aaagtaaggt aagcacggag ttgagtgccg gatagcggcg gacgggtgag taacgcgtgg      180
gcaacctacc cttaagaccg ggataacacc tcgaaagggg tgctaatact ggataagctc      240
cttgtagggc atcctatgag gagggaaggt agcggaagct accgcttaag gatgggcccg      300
cgtcccatca gctagttggt agggtaacgg cctaccaagg cgacgacggg tagccggcct      360
gagagggtgg tcggccacac tgggactgag acacggccca gactcctacg ggaggcagca      420
gtggggaatc ttgcgcaatg ggcgaaagcc tgacgcagcg acgccgcgtg agcgaagaag      480
gccttcgggt cgtaaagctc gatagtgtgg gaagaataga tgacggtacc acacgaaagc      540
cccggctaac tacgtgccag cagccgcggt aagacgtagg gggcgagcgt tgtccggaat      600
tactgggcgt aaagggcgcg taggcggcca cttaagtcag gtgtaaaaaa cccgggctca      660
acccggggga tgcacatgaa actgggtggc tagagggcag gagaggggag tggaattccc      720
ggtgtagcgg tgaaatgcgt agatatcggg aggaatacca gtggcgaagg cgactctctg      780
gactgacccct gacgctgagg cgcgaaagcg tggggagcaa acaggattag ataccctggt      840
agtccacgcc gtaaacgatg gtactaggt gtgggatgcg gaagcattcc gtgccgtagt      900
taacgcaata agtaccccgc ctggggagta cggccgcaag gttgaaactc aaaggaattg      960
acggggcccc gcacaagcgg tggagcatgt ggtttaattc gaagcaacgc gaagaacctt     1020
accagggctt gacatgcagg tagtagcgag ccgaaaggtg agcgacccgg cactcaagtg     1080
```

<210> SEQ ID NO 12
<211> LENGTH: 1451
<212> TYPE: DNA
<213> ORGANISM: Artificial Sequence
<220> FEATURE:
<223> OTHER INFORMATION: 16SrDNA from Thermoanaerobacter sp. DIB101X

<400> SEQUENCE: 12

```
gccccacttt cgacggctcc ctccttcccg gttgggtcac cggcttcggg tgtcgcaggc       60
tctcgtggtg tgacgggcgg tgtgtacaag gcccgggaac gtattcaccg cggcatgctg      120
atccgcgatt actagcgatt ccgacttcat gcaggcgagt tgcagcctgc aatccgaact      180
tggaccggct ttttgggatt cgctccgcct cgcggcttcg cttccctctg taccggccat      240
tgtagcacgt gtgtggccca gggcatatag ggcatgatga tttgacgtca tccccacctt      300
cctccgtgtc ctccacggca gtccctctag agtgcccggc ttacccgctg gcaactagag      360
gcaggggttg cgctcgttgc gggacttaac ccaacatctc acgacacgag ctgacgacaa      420
ccatgcacca cctgtgcagg ctccttacct cccggtaagg tcgctcccct ttcggttcgc      480
tactacctgc atgtcaagcc ctggtaaggt tcttcgcgtt gcttcgaatt aaaccacatg      540
ctccaccgct tgtgcgggcc ccgtcaatt cctttgagtt tcaaccttgc ggccgtactc      600
cccaggcggg gtacttattg cgttcgctac ggcacggaac gcttccgcgc cccacaccta      660
```

| | |
|---|---|
| gtacccatcg tttacagcgt ggactaccag ggtatctaat cctgttcgct ccccacgctt | 720 |
| tcgcgcctca gcgtcagggc cagtccagag agtcgccttc gccactggta ttcctcccga | 780 |
| tatctacgca tttcaccgct acaccgggaa ttccactccc ctctcctgcc ctctagccaa | 840 |
| tcagtttcag atgctacccc cggggttgagc ccgggtctttt tacacctgac ttgattgacc | 900 |
| gcctacgcgc cctttacgcc cagtaattcc ggacaacgct cgcccctac gtcttaccgc | 960 |
| ggctgctggc acgtagttag ccggggcttt cgtgtggtac cgtcatccct tcttcccaca | 1020 |
| ctaacggggt ttacaacccg aaggccttcc tcccccacgc ggcgtcgctg ggtcaggctt | 1080 |
| ccgcccattg cccaagattc cccactgctg cctcccgtag gagtctgggc cgtgtctcag | 1140 |
| tcccagtgtg gccgaccacc ctctcaggcc ggctacccgt cgtcgccttg gtaggccgtt | 1200 |
| accctaccaa ctagctgatg ggacgcgggc ccatccttaa gcggtagctt gcgcctccct | 1260 |
| ttcctcccta taggatgccc tataaggagc ttatccagta ttaccacccc tttcgaggtg | 1320 |
| ctatcccggt cttaagggta ggttgcccac gcgttactca cccgtccgcc gctatccgcc | 1380 |
| acccaactac gttgagtgcc ggaccgctcg acttgcatgt gttaggcacg ccgccagcgt | 1440 |
| tcgtcctgag c | 1451 |

<210> SEQ ID NO 13
<211> LENGTH: 1465
<212> TYPE: DNA
<213> ORGANISM: Artificial Sequence
<220> FEATURE:
<223> OTHER INFORMATION: 16SrDNA from Thermoanaerobacter sp. DIB103X

<400> SEQUENCE: 13

| | |
|---|---|
| ttcaccccaa tcacctgccc caccttcgac ggctccctcc tccccggttg ggtcaccggc | 60 |
| ttcgggtgtc gcaggctctc gtggtgtgac gggcggtgtg tacaaggccc gggaacgtat | 120 |
| tcaccgcggc atgctgatcc gcgattacta gcgattccga cttcatgcag gcgagttgca | 180 |
| gcctgcaatc cgaacttgga ccggcttttt gggattcgct ccgcctcgcg gcttcgctcc | 240 |
| cctctgtacc ggccattgta gcacgtgtgt ggcccagggc atatagggca tgatgatttg | 300 |
| acgtcatccc caccttcctc cgtgtcctcc acggcagtcc cctagagtg cccggcttac | 360 |
| ccgctggcaa ctagaggcag gggttgcgct cgttgcggga cttaacccaa catctcacga | 420 |
| cacgagctga cgacaaccat gcaccacctg tgcaggctcc ttacctcccg gtaaggtcgc | 480 |
| tccccttcg gttcgctact acctgcatgt caagccctgg taaggttctt cgcgttgctt | 540 |
| cgaattaaac cacatgctcc accgcttgtg cgggcccccg tcaattcctt tgagtttcaa | 600 |
| ccttgcggcc gtactcccca ggcggggtac ttattgcgtt cgctacggca cggaacgctt | 660 |
| ccgcgcccca cacctagtac ccatcgttta cagcgtggac taccagggta tctaatcctg | 720 |
| ttcgctcccc acgctttcgc gcctcagcgt cagggccagt ccagagagtc gccttcgcca | 780 |
| ctggtattcc tcccgatatc tacgcatttc accgctacac cgggaattcc actcccctct | 840 |
| cctgccctct agccaatcag tttcagatgc tacccccggg ttgagcccgg tcttttaca | 900 |
| cctgacttga ttgaccgcct acgcgccctt tacgcccagt aattccggac aacgctcgcc | 960 |
| ccctacgtct taccgcggct gctggcacgt agttagccgg ggctttcgtg tggtaccgtc | 1020 |
| atcccttctt cccacactaa cggggtttac aacccgaagg ccttcctccc cacgcggcg | 1080 |
| tcgctgggtc aggcttccgc ccattgccca agattcccca ctgctgcctc ccgtaggagt | 1140 |
| ctgggccgtg tctcagtccc agtgtggccg accaccctct caggcggct acccgtcgtc | 1200 |
| gccttggtag gccgttaccc taccaactag ctgatgggac gcgggcccat ccttaagcgg | 1260 |

```
tagcttgcgc ctcccttcc tccctatagg atgccctata aggagcttat ccagtattac    1320 caccccttc gaggtgctat cccggtctta agggtaggtt gcccacgcgt tactcacccg    1380
tccgccgcta tccgccaccc aactacgttg agtgccggac cgctcgactt gcatgtgtta    1440
ggcacgccgc cagcgttcgt cctga                                         1465
```

<210> SEQ ID NO 14
<211> LENGTH: 1665
<212> TYPE: DNA
<213> ORGANISM: Artificial Sequence
<220> FEATURE:
<223> OTHER INFORMATION: 16SrDNA from Thermoanaerobacter sp. DIB104X

<400> SEQUENCE: 14

```
actcaagtgg gcacgttttt ttctcttcat cacgtttcta acatgcccac ttgagtgccg      60
ggttgggtca ccggcttcgg gtgttgcaga ctctcgtggt gtgacgggcg gtgtgtacaa     120
ggcccgggaa cgtattcacc gcggcatgct gatccgcgat tactagcgat tccgacttca    180
tgcaggcgag ttgcagcctg caatccgaac ttggaccggc tttttggggt ccgctccaga    240
tcgctccttc gcctccctct gtaccggcca ttgtagcacg tgtgtggccc agggcatata    300
gggcatgatg atttgacgtc atccccacct tcctccgtgt tgtccacggc agtccctcta    360
gagtgcctcc gtcactcaac tgaacacgct atcccttcct ctctactctt tcctaacatg    420
ttcagttgag tgacggactg gcaactagaa gcaagggttg cgctcgttgc gggacttaac    480
ccaacatctc acgacacgag ctgacgacaa ccatgcacca cctgtgcagg ctcccggcac    540
tcaagtaggc acttcattct ccctcttact accttctcta tcatgcccac ttgagtgccg    600
ggtcgctcac ctttcggctc gctactacct gcatgtcaag ccctggtaag gttcttcgcg    660
ttgcttcgaa ttaaaccaca tgctccaccg cttgtgcggg ccccgtcaa ttcctttgag     720 tttcaacctt gcggccgtac tccccaggcg gggtacttat tgcgttaact acggcacgga    780
atgcttccgc atcccacacc tagtacccat cgtttacggc gtggactacc agggtatcta    840
atcctgtttg ctccccacgc tttcgcgcct cagcgtcagg gtcagtccag agagtcgcct    900
tcgccactgg tattcctccc gatatctacg catttcaccg ctacaccggg aattccactc    960
ccctctcctg ccctctagcc acccagtttc atgtgcatcc cccgggttga gcccgggttt   1020
tttacacctg acttaagtgg ccgcctacgc gcccttacg cccagtaatt ccggacaacg     1080
ctcgccccct acgtcttacc gcggctgctg gcacgtagtt agccggggct ttcgtgtggt    1140
accgtcatct attcttccca cactatcgag ctttacgacc cgaaggcctt cttcgctcac    1200
gcggcgtcgc tgcgtcaggc tttcgcccat tgcgcaagat tccccactgc tgcctcccgt    1260
aggagtctgg gccgtgtctc agtcccagtg tggccgacca cctctcagg ccggctaccc     1320 gtcgtcgcct tggtaggccg ttaccctacc aactagctga tgggacgcgg gcccatcctt    1380
aagcggtagc ttccgctacc ttccctcctc ataggatgcc ctacaaggag cttatccagt    1440
attagcaccc ctttcgaggt gttatcccgg tcttaagggt aggttgccca cgcgttactc    1500
acccgtccgc cgctatccgg cactcaactc cgtgcttacc ttactttgca ccactttat    1560 tactttcttc ttctactata cttccttccc cttaagtaag cacttagttg agtgccggac    1620
cgctcgactt gcatgtgtta ggcacgccgc cagcgttcgt cctga                   1665
```

<210> SEQ ID NO 15
<211> LENGTH: 1105
<212> TYPE: DNA

<213> ORGANISM: Artificial Sequence
<220> FEATURE:
<223> OTHER INFORMATION: 16SrDNA from Thermoanaerobacter sp. DIB107X

<400> SEQUENCE: 15

```
tcaggacgaa cgctggcggc gtgcctaaca catgcaagtc gagcggtccg gcactcaacg      60
tagttgagtg gcggatagcg gcggacgggt gagtaacgcg tgggcaacct acccttaaga     120
ccgggatagc acctcgaaag gggtggtaat actggataag ctcccttatag ggcatcctat    180 agggaggaaa gggaagcgca agctaccgct taaggatggg cccgcgtccc atcagctagt    240
tggtagggta acggcctacc aaggckacga cgggtagccg gcctgagagg gtggtcggcc    300
acactgggac tgagacacgg cccagactcc tacgggaggc agcagtgggg aatcttgggc    360
aatgggcgga agcctgaccc agcgacgccg cgtgggggag gaaggccttc gggttgtaaa    420
ccccgttagt gtgggaagaa gggatgacgg taccacacga aagccccggc taactacgtg    480
ccagcagccg cggtaagacg taggggggcga gcgttgtccg gaattactgg gcgtaaaggg    540
cgcgtaggcg gtcaatcaag tcaggtgtaa aagacccggg ctcaacccgg gggtagcacc    600
tgaaactggt tggctagagg gcaggagagg ggagtggaat tcccggtgta gcggtgaaat    660
gcgtagatat cgggaggaat accagtggcg aaggcgactc tctggactgg ccctgacgct    720
gaggcgcgaa agcgtgggga gcaacagga ttagataccc tggtagtcca cgctgtaaac    780
gatgggtact aggtgtgggg cgcggaagcg ttccgtgccg tagcgaacgc aataagtacc    840
ccgcctgggg agtacggccg caaggttgaa actcaaagga attgacgggg gcccgcacaa    900
gcggtggagc atgtggttta attcgaagca acgcgaagaa ccttaccagg gcttgacatg    960
caggtggtag cgaaccgaaa ggtgagcgac cttaccggga ggtaaggagc ctgcacaggt   1020
ggtgcatggt tgtcgtcagc tcgtgtcgtg agatgttggg ttaagtcccg caacgagcgc   1080 aaccctgcc tctagttgcc agcgg                                           1105
```

<210> SEQ ID NO 16
<211> LENGTH: 20
<212> TYPE: DNA
<213> ORGANISM: Artificial Sequence
<220> FEATURE:
<223> OTHER INFORMATION: 27F forward primer

<400> SEQUENCE: 16

```
agagtttgat cmtggctcag                                                  20
```

<210> SEQ ID NO 17
<211> LENGTH: 19
<212> TYPE: DNA
<213> ORGANISM: Artificial Sequence
<220> FEATURE:
<223> OTHER INFORMATION: 1492R reverse Primer

<400> SEQUENCE: 17

```
ggttaccttg ttacgactt                                                   19
```